United States Patent [19]

Kresch et al.

[11] Patent Number: 5,527,331
[45] Date of Patent: Jun. 18, 1996

[54] METHOD FOR PROSTATIC TISSUE RESECTION

[75] Inventors: Arnold J. Kresch, Portola Valley; Donald L. Alden, Sunnyvale, both of Calif.

[73] Assignee: FemRx, Sunnyvale, Calif.

[21] Appl. No.: 529,144

[22] Filed: Sep. 15, 1995

Related U.S. Application Data

[63] Continuation of Ser. No. 322,680, Oct. 13, 1994, which is a continuation-in-part of Ser. No. 136,426, Oct. 13, 1993, Pat. No. 5,456,689.

[51] Int. Cl.$^6$ .................................................. A61B 17/00
[52] U.S. Cl. .......................... 606/170; 606/180; 606/45; 604/22
[58] Field of Search .................... 606/1, 13–15, 606/159, 170, 171, 167, 180, 37, 46; 128/3, 4, 6, 751–755, 898; 604/22, 24 AA

[56] References Cited

U.S. PATENT DOCUMENTS

| | | |
|---|---|---|
| 3,942,530 | 3/1976 | Northeved . |
| 4,132,227 | 1/1979 | Ibe . |
| 4,149,538 | 4/1979 | Mrava et al. . |
| 4,362,160 | 12/1982 | Hiltebrandt . |
| 4,756,309 | 7/1988 | Sachse et al. . |
| 4,936,281 | 6/1990 | Stasz . |
| 4,986,825 | 1/1991 | Bays et al. . |
| 4,998,527 | 3/1991 | Meyer . |
| 5,133,713 | 7/1992 | Huang et al. . |
| 5,176,677 | 1/1993 | Wuchinich . |
| 5,201,731 | 4/1993 | Hakky . |
| 5,312,399 | 5/1994 | Hakky et al. ......................... 606/170 |
| 5,313,949 | 5/1994 | Yock . |
| 5,325,860 | 7/1994 | Seward et al. . |
| 5,335,663 | 8/1994 | Oakley et al. . |

Primary Examiner—Stephen C. Pellegrino
Assistant Examiner—William Lewis
Attorney, Agent, or Firm—Townsend and Townsend and Crew

[57] ABSTRACT

A tissue resection device for preferred use in an organ inflated with non-conductive optically transparent fluid under pressure is disclosed. The instrument includes a rigid shaft having a proximal end, a distal end, and defining a perfusion lumen extending therebetween. At its distal end, the shaft is provided with a rounded blunt end having an elongate aperture exposing the lumen near the distal end. A drive tube is rotatably disposed within the shaft lumen and has a proximal end, a distal end, and a drive tube aspiration lumen extending therebetween. A cutting head is mounted on the distal end of the drive tube and has a laterally disposed cutting edge which can resection either by conventional cutting or electrocautery. This laterally disposed cutting edge is communicated to an internal passage between the cutting edge and the aspiration lumen of the drive tube so that tissue severed as the cutting head is rotated may be drawn directly into the aspiration lumen. A housing attached to the proximal end of the shaft. Preferably, a DC motor in the housing is connected to rotate the drive tube and thus the laterally disposed cutting head. Connection is provided on the housing for connecting the perfusion shaft lumen to a perfusion source and the aspiration lumen to an aspiration source. Preferably, an optic fiber provides an optical view of surgery while a proximally mounted and laterally exposed ultrasound transducer is disposed with a solid angle of interrogation including the surgical site.

20 Claims, 16 Drawing Sheets

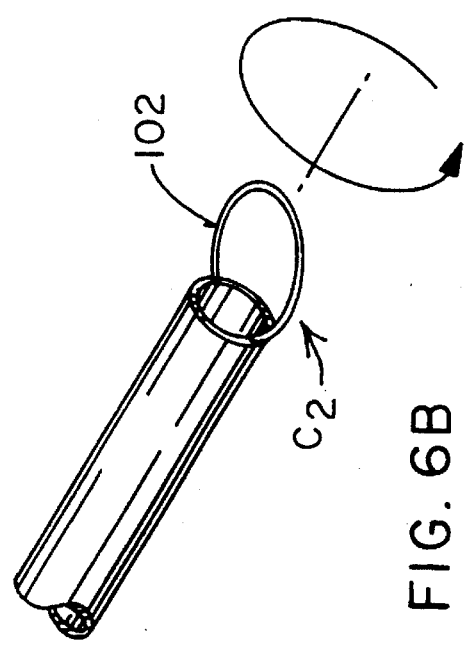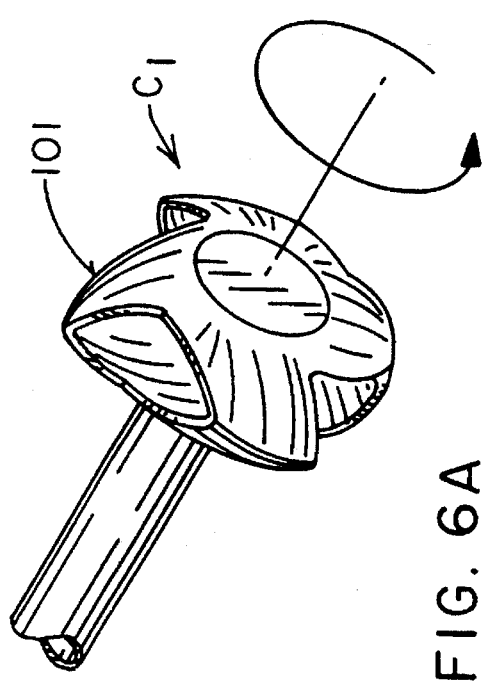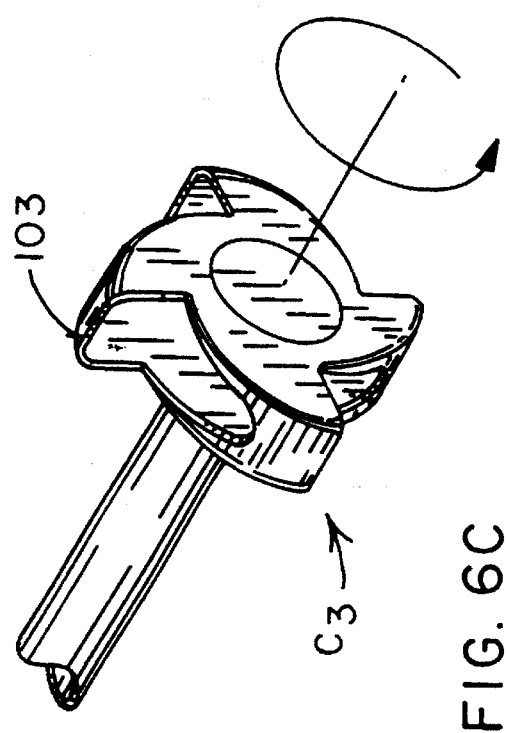
FIG. 6B
FIG. 6A
FIG. 6C

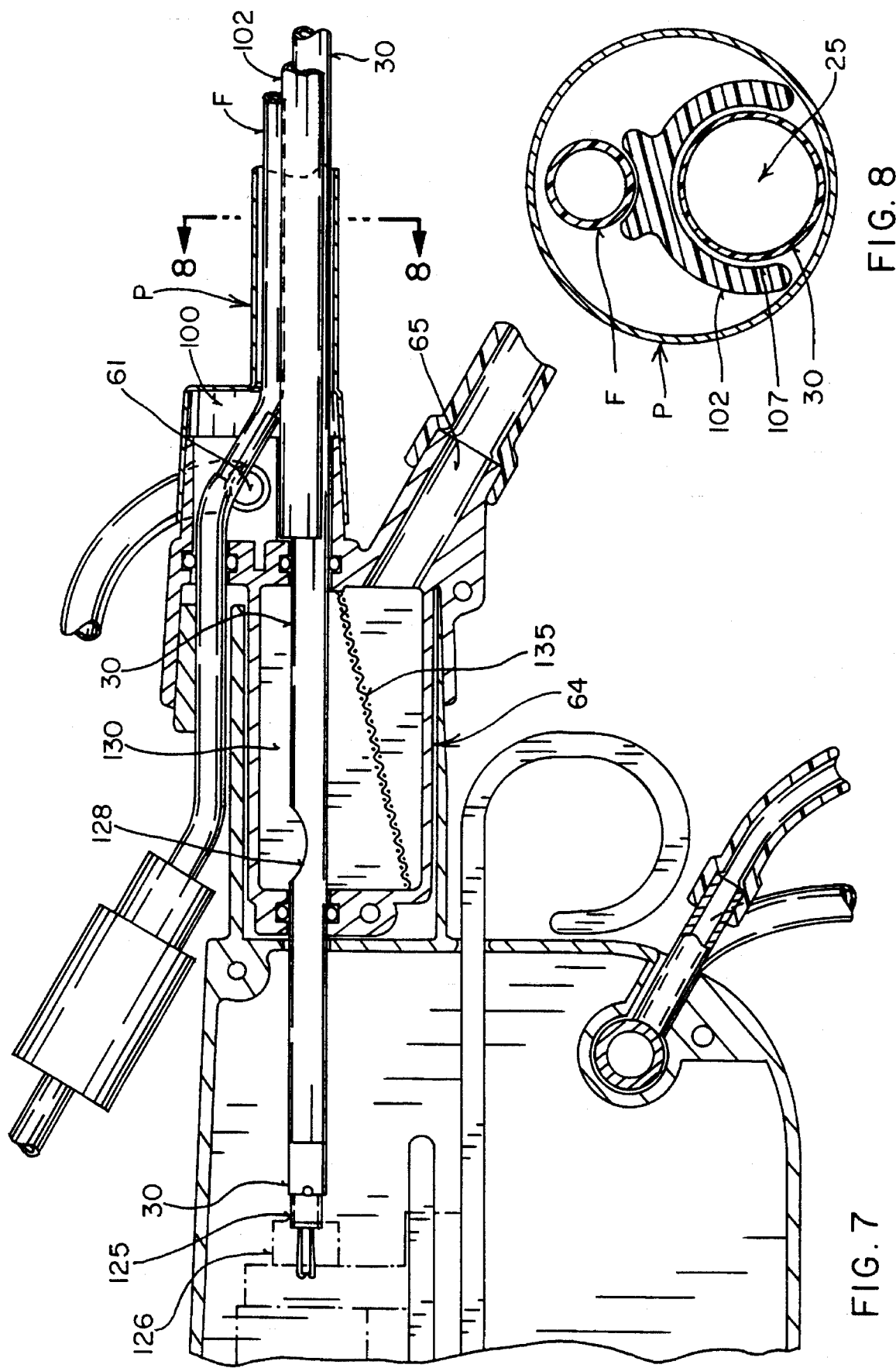

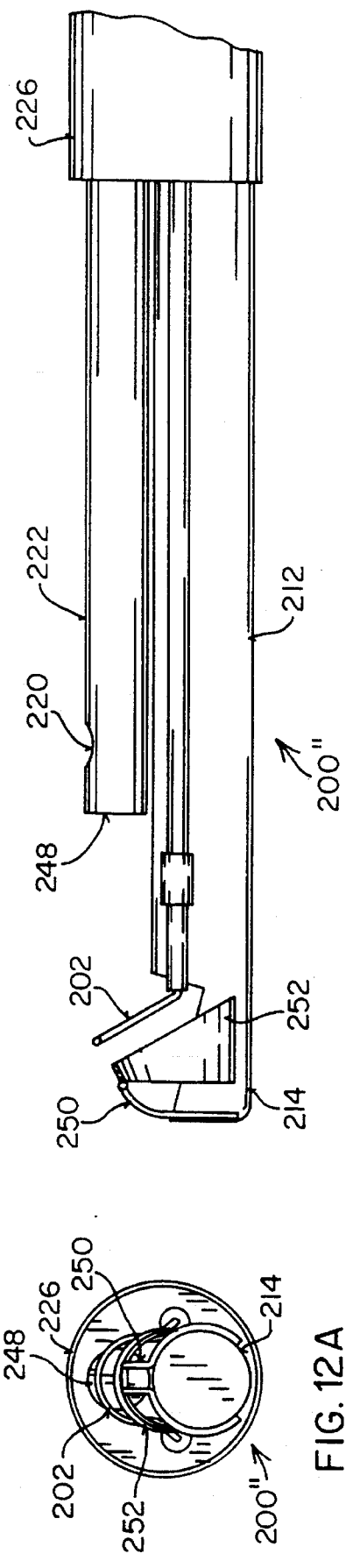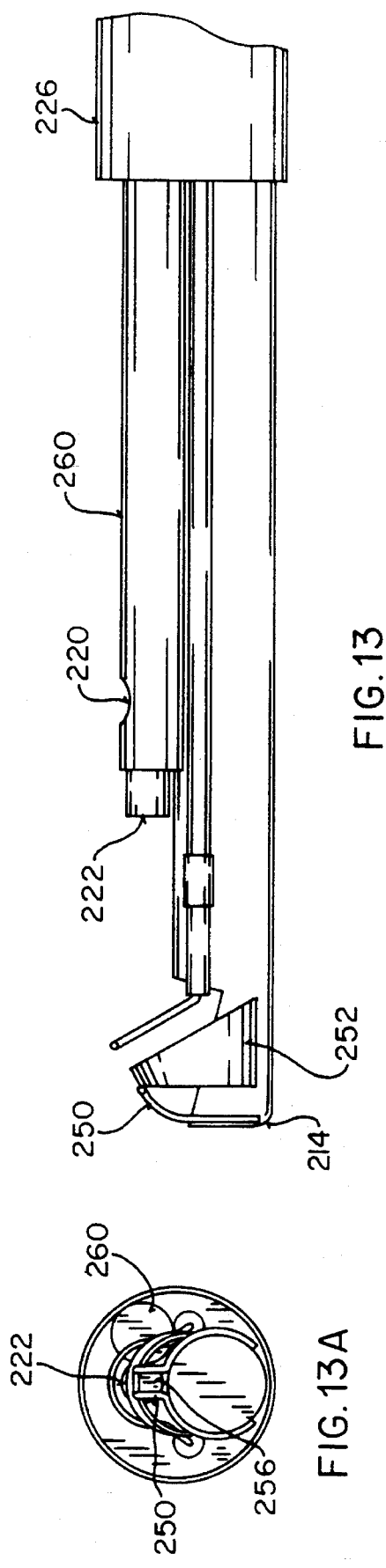

METHOD FOR PROSTATIC TISSUE RESECTION

CROSS REFERENCE TO RELATED APPLICATIONS

This application is a continuation of U.S. patent application Ser. No. 08/322,680, filed Oct. 13, 1994, which is a continuation-in-part of U.S. patent application Ser. No. 08/136,426, filed Oct. 13, 1993, now U.S. Pat. No. 5,456,689 the full disclosures of which are herein incorporated by reference.

BACKGROUND OF THE INVENTION

This invention relates to a method and device for tissue resection, especially surgical treatment of the uterus or prostate.

Electrocautery has been in use for many years as a general surgical tool, such as for trans-cervical fibroid removal. The uterus is first flooded under pressure with a non-conductive sorbitol-mannitol fluid under sufficient pressure to separate the walls of the uterus and render the surgical site suitable for optical fiber observation under a procedure generally described as uterine cavity distention. During this flooding, an electrocautery surgical tool is inserted into the uterus through the cervix. Electrical current at high power settings (an alternating current about 750 KHz) is transmitted from the cutting surface of the surgical instrument to the surgical site. The cutting surface usually consists of a wire or solid shape. The transmission of current to the uterus is monopolar and completed by a conductive path to the power unit through a conductive pad applied to the patient's skin.

The electrical current is concentrated at the cutting surface. Heat generated from the resistance of tissue to the flow of electrical current is high enough to vaporize cells near the cutting surface. Thus a cut is made with very little physical resistance to the cutting action. Heat from the cut cauterizes small blood vessels so that visibility and control remain good.

In the cautery mode and during uterine cavity distention, the same electrical resistance heating is used at lower power settings to cauterize tissue and to kill selected areas. Cautery electrodes can be larger in area so as to treat broader surfaces. Cautery is used in gynecology to ablate the endometrial lining of the uterus. This procedure is often performed using a conductive roller similar in shape to a football which heats a wide swath along the inner surface of the uterus.

Electrocautery tools are compact and require a minimum of area in which to work. Since the tool only cuts when the power is turned on, they can be safely maneuvered into small areas. Electrocautery has found broad general application in the treatment of enlarged prostate glands, and in the removal of uterine fibroids.

A secondary effect of the removal of tissue, particularly in the areas of prostate reduction and fibroid removal, is that severed morsels remain in the working area and must be periodically flushed or suctioned away to preserve the required visibility necessary for surgery. The clean, well controlled action of electrocautery is now slowed by the need to remove fragments which obstruct visibility. This required removal prolongs the surgical procedure.

It is known that ultrasound can add significant value to tissue resection and ablation procedures. Using high-frequency ultrasound, anatomical landmarks and tissue features can be imaged in depth, which cannot be done by optical instruments. Depth information provides improved guidance and monitoring capabilities. It enables the surgeon to monitor the progress of tissue treatment, and thereby lessens the risk of complications. In addition, the improved visualization provided by ultrasound can help to shorten procedure times.

At the present time as for example during uterine cavity distention, it is not practical to introduce ultrasound probes without considerable complication.

To perform ultrasound measurements during electrocautery, the surgical probes for the electrocautery procedure must first be removed and thereafter, ultrasound introduced. Finally, and after such measurements, surgery can resume with reintroduction of the surgical probes. With such procedures, the surgeon has difficulty returning to the original surgical site. For this reason, ultrasound is not usually utilized for measurement of uterine wall thickness by an intrauterine transducer.

SUMMARY OF THE INVENTION

A tissue resection device for preferred use in an organ inflated with substantially non-conductive optically transparent fluid under pressure is disclosed. The instrument includes a rigid shaft having a proximal end, a distal end, and defining a perfusion lumen extending therebetween. At the distal end of the shaft, the shaft is provided with a rounded blunt end having an elongate aperture exposing the lumen near the distal end. A removable drive tube is rotatably disposed within the shaft lumen and has a proximal end, a distal end, and a drive tube aspiration lumen extending therebetween. A cutting head is mounted on the distal end of the drive tube and has a laterally disposed cutting edge which can resect either by conventional cutting or electrocautery. This laterally disposed cutting edge is communicated to an internal passage between the cutting edge and the aspiration lumen of the drive tube so that tissue severed as the cutting head is rotated may be drawn directly into the aspiration lumen. A housing is attached to the proximal end of the shaft. Preferably, a DC motor in the housing is connected to rotate the drive tube and thus the laterally disposed cutting head. Connection is provided on the housing for connecting the perfusion shaft lumen to a perfusion source and the aspiration lumen to an aspiration source. Preferably, an optic fiber or hysteroscope at the proximal end of the elongate aperture of the shaft provides illumination and an optical view of surgery while a distally mounted and laterally exposed ultrasound transducer is disposed with a solid angle of interrogation including the surgical site. The surgical instrument finds preferred use in the uterus during uterine cavity distention where surgery occurs at the cutting head and can be disposable. During the surgical process, the cutting head is preferably drawn distally of the elongate cutting aperture towards the viewing optical fiber with the ultrasound transducer positioned to acoustically interrogate the operative site immediately after surgery.

A novel feature of this design is that the morsels removed by the cutter are extracted immediately through the aspiration lumen in the rotating shaft. Controlling the size of the chips, and directing them into the shaft center is achieved through the design of the cutter head. Controlled aspiration, typically by a finger actuated valve, occurs from within the cutter head to a retain sieve. Vision of the surgical site is improved.

Another novel feature of this design is a removable and disposable cartridge which surrounds the rotating cutter shaft where it enters the handle, and filters the surgical debris from the sorbitol-mannitol fluid used in the uterine cavity during the procedure for distention and visualization. The removed tissue is contained in the cartridge which can be sent intact to a laboratory for examination.

A feature of this design is that the handle, external shaft, and motor assembly can be re-used allowing for cost savings. The cutter head and shaft are intended to be disposable and can quickly plug into the handle assembly.

Another feature of this design is that a variety of cutter head configurations can be built which will allow for greater flexibility and effectiveness in treatments. A few examples are: an end-effect cutter for removing tissue at the end of the cutter axis; a smooth, or textured, head for ablation of uterine lining; and a narrow cutter for trimming the edge of a feature, or for cutting into a restricted area.

Another feature of this design is the control which is provided by the motorized operation. In conventional procedures, a surgeon is required to expend coordinated effort in moving and extracting debris in addition to actually making a series of cuts. With the motorized cutter and extraction system, the surgeon directs the cutter head to the area to be treated, and slowly draws the cutter through the fibroid to be removed. A trigger attached to the driving motor enables the cutting head to traverse the elongate aperture, preferably from the distal end to the proximal end toward the viewing fiber. Cutting is a matter of pressure and time at any particular area, and the feedback of the results is immediate through both visual observation and ultrasound interrogation in the wake of the resection. Fatigue is reduced, allowing for more precise work.

Another feature of this design is the ability to vary the motor speed and direction. Low speed cutting is more accurate and offers better control. Where a cutter head with electrocautery cutting edges is utilized, stopping or reversing the rotation offers the ability to treat the surface of an organ or to cauterize an area which is bleeding.

Another feature of this design is the use of the journal bearing as an electrical contact for the high voltage cutting current. This eliminates the need for a large slip-ring assembly, making the handle more compact and less expensive.

Yet another feature of this design is the mounting of the probe to a base unit adapted for fitting to the hand of the surgeon. Typically, the body of the drive unit is grasped between the hand and thumb. The forefinger (trigger finger) is utilized to cause the cutting head to traverse the elongate aperture for cutting at the surgical site. Motion of the housing directs the distal end of the probe to the surgical site.

Another feature of this design is the incorporation of the aspiration control valve into the handle. The valve is positioned so that it can be operated with one finger while steadying the tool and controlling the motion of the cutter with the rest of the hand. Aspiration can be made as vision and surgery requires with infusion through the instrument maintaining require cavity pressure.

Another feature of this design is that the cutter head and shaft, and scope can be removed from the outer sheath to allow the use of an obturator for dilating the cervix and introducing the sheath.

An added advantage of this invention is the incorporation of a sound transducer to the cutting head. Such a transducer can measure remaining organ wall thickness, preferably immediately after surgery. Surgery can be conveniently limited to avoid damage to adjacent organs.

The invention further provides an exemplary method for resecting tissue from a patient's internal body structure. According to the method, the depth of tissue to be resected is ultrasonically measured, and the tissue is removed from the internal body structure. In a preferable aspect, the removed tissue is chopped into smaller morsels which are then evacuated from the patient.

In one particular aspect of the method, the tissue is electrosurgically removed by translating an electrosurgical wire along and through the tissue. In this way, the tissue is removed in elongate strips which can then by chopped into smaller morsels by rotating a sharpened blade in the uterus. In another particular aspect, the internal body structure is optically visualized while removing the tissue. In still another aspect, bleeding tissue on the internal body structure is cauterized.

The invention provides another exemplary method for resecting tissue from a patient's internal body structure by directing an electrosurgical member into the tissue and translating the electrosurgical member through the tissue to electrosurgically remove tissue from the internal body structure. The removed tissue is then chopped into smaller morsels. Once the tissue is reduced in size, the morsels are evacuated from the patient. In a preferred aspect, the electrosurgical member is an electrosurgical wire which is translated to remove the tissue in elongate strips. Simultaneously, a sharpened blade is rotated in the internal body structure to chop the removed tissue into smaller morsels for evacuation.

In a particularly preferable aspect, the depth of tissue to be removed is measured by use of an ultrasonic transducer. In another aspect, the internal body structure is optically visualized. In a further aspect, bleeding tissue on the internal body structure is cauterized.

In yet another method of the invention, tissue is resected from a body structure by providing a probe having a proximal end, a distal end, a lumen extending therebetween, and an aperture exposing the lumen near the distal end. An electrosurgical wire is also provided near the distal end of the probe, and a drive member is rotatably disposed within the probe lumen. A rotatable cutting member is provided at the distal end of the drive member with the cutting member being accessible through the aperture. The probe is positioned at a surgical site near the body structure, and the electrosurgical wire is translated along tissue at the surgical site to resect tissue from the body structure. To chop the removed tissue into smaller morsels, the cutting member is rotated as the tissue is directed into the cutting member.

In one particular aspect, the morsels are aspirated from the body structure through the probe lumen. In another aspect, the depth of tissue resection is ultrasonically viewed. In still anther aspect, an electrically conductive element on the probe is provided with current, and the electrically conductive element is placed against bleeding tissue on the body structure to effect cauterization.

The invention provides an alternative embodiment of tissue resection device which includes an elongate body having a proximal end and a distal end. Means is provided near the distal end for electrosurgically removing tissue, and an ultrasonic transducer is disposed on the device for ultrasonically imaging tissue at a surgical site to determine depth of tissue to be resected. In a particularly preferable aspect, the ultrasonic transducer is held in an axially translatable shaft disposed adjacent the elongate body. In this way, translation of the shaft moves the transducer to a desired imaging site.

In one aspect, the elongate body includes a lumen extending between the proximal and the distal ends and an aperture exposing the lumen near the distal end. Means is provided for evacuating resected tissue through the lumen. To assist in the evacuation of tissue, means is provided in the lumen for chopping resected tissue into smaller morsels. Preferably, the chopping means includes a rotatable cutting member.

In yet another aspect, means for directing removed tissue to the chopping means is provided. Preferably, the directing means includes an extension on the distal end of the elongate body.

In still another aspect, an optical fiber is provided and includes a viewing end disposed near the wire. The optical fiber is preferably held in a translatable shaft adjacent the elongate member. In this way, cutting of tissue with the wire may be observed through the optical fiber. The directing means can also be provided with an aperture that is aligned with the viewing end of the optical fiber so that tissue beyond the distal end of the elongate body may be observed through the optical fiber. In one aspect, at least a portion of the directing means is electrically conductive so that electrocauterization of tissue can be effected upon contact with the directing means.

The invention provides yet a further alternative embodiment of a tissue resection device that includes an elongate body having a proximal end and a distal end. An electrosurgical wire is disposed near the distal end of the elongate body, and chopping means is disposed near the distal end of the elongate body for chopping resected tissue into smaller morsels. A housing is attached to the proximal end of the elongate body, and means is disposed in the housing for actuating the chopping means.

In a preferable aspect, an ultrasonic transducer is disposed near the wire for ultrasonically imaging depth of tissue resection at a surgical site. Preferably, the ultrasonic transducer is held in an axially translatable shaft disposed adjacent the elongate body so that translation of the shaft moves the transducer to a desired imaging site.

In another aspect, means is provided for directing removed tissue to the chopping means. The directing means in one aspect preferably includes an extension on the distal end of the elongate body.

An optical fiber having a viewing end disposed near the wire can also be provided for observing the cutting of tissue or for positioning of the electrocautery wire. In one aspect, the directing means includes an aperture that is aligned with the viewing end of the optical fiber so that tissue beyond the distal end of the elongate body may be observed through the optical fiber.

In still another aspect, the elongate body includes a central lumen and an aperture exposing the lumen near the distal end of the elongate body. The chopping means, which preferably includes a rotatable cutting member, is disposed in the central lumen and is accessible through the aperture. Aspiration means is provided for aspirating the chopped tissue through the central lumen, and in a further aspect at least a portion of the directing means is electrically conductive so that electrocauterization of tissue can be effected upon contact with the directing means.

In one particular embodiment, the invention provides for a diagnostic device that can be used to diagnose abnormalities in the endometrial cavity or the uterine wall. Diagnosis is accomplished by mapping the uterus from within the endometrial cavity. According to this method, an ultrasonic transducer is introduced into the endometrial cavity. The transducer is then actuated at various positions within the endometrial cavity to measure the thickness of the uterine wall. The measurements are then processed to produce a map of the uterus. The map can then be evaluated to diagnose any abnormalities.

BRIEF DESCRIPTION OF THE DRAWINGS

Other objects, features and advantages of this surgical instrument and accompanying procedure will become more apparent after referring to the following specification and attached drawings in which:

FIGS. 6A–6C are differing cutting heads utilized with this instrument;

FIG. 7 is a detail of the probe at the point of attachment to the housing illustrating the disposition of the sieve for capture of the chips or morsels from surgery and illustrating how the disposable probe can be shipped (intact or bent) for compact shape for transport for biopsy of the retained chips or morsels;

FIG. 8 is a section along lines 8—8 of FIG. 7 illustrating both the perfusion path and the aspiration path together with the relative locations of the probe, rotating tube, and path for the viewing optical fiber;

FIG. 12 is an alternative embodiment of the device of FIG. 11 employing a wire director for directing removed tissue into the chopping mechanism;

FIG. 12A is a front end view of the device of FIG. 12;

FIG. 13 illustrates an alternative embodiment of the device of FIG. 12 with the optical scope and the ultrasonic transducer being separated;

FIG. 13A is a front end view of the device of FIG. 13; and

DESCRIPTION OF THE PREFERRED EMBODIMENT

Figure 1A:
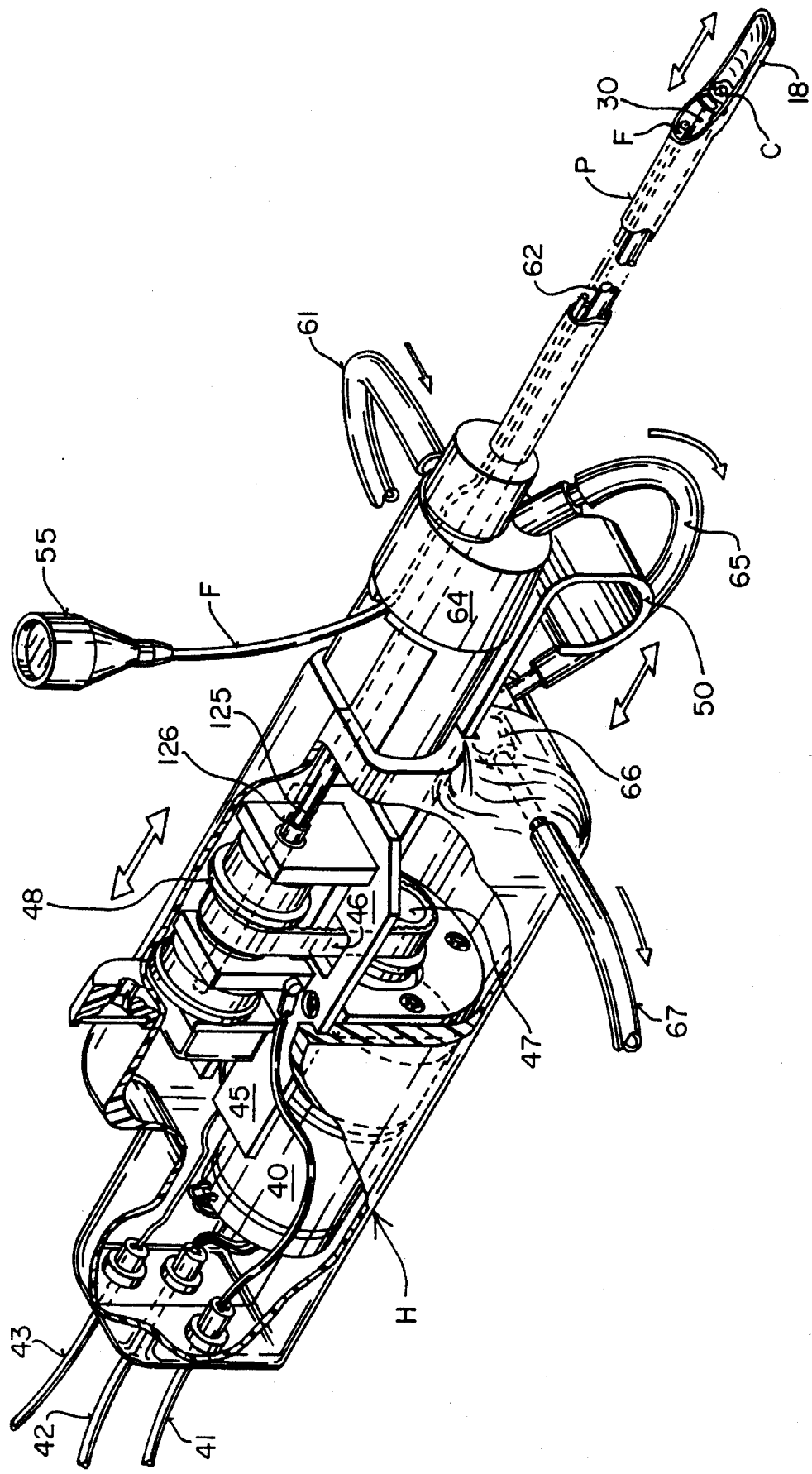
FIG. 1A is a perspective view of the drive housing with probe attached illustrating the housing and probe in partial section for understanding of the operative portions of the instrument.

Referring to FIG. 1A, surgical probe P is shown mounted to housing H. In understanding this invention, the probe P will first be discussed with respect to the preferred embodiment of FIGS. 2A and 2B. Thereafter, the construction and operation of the probe from drive housing H in the hand of a surgeon will be discussed. Finally, alternate embodiments of the probe and cutting head as well as the capture of chips or morsels from the surgical site within the detachable probe will be set forth.

Figure 2A:
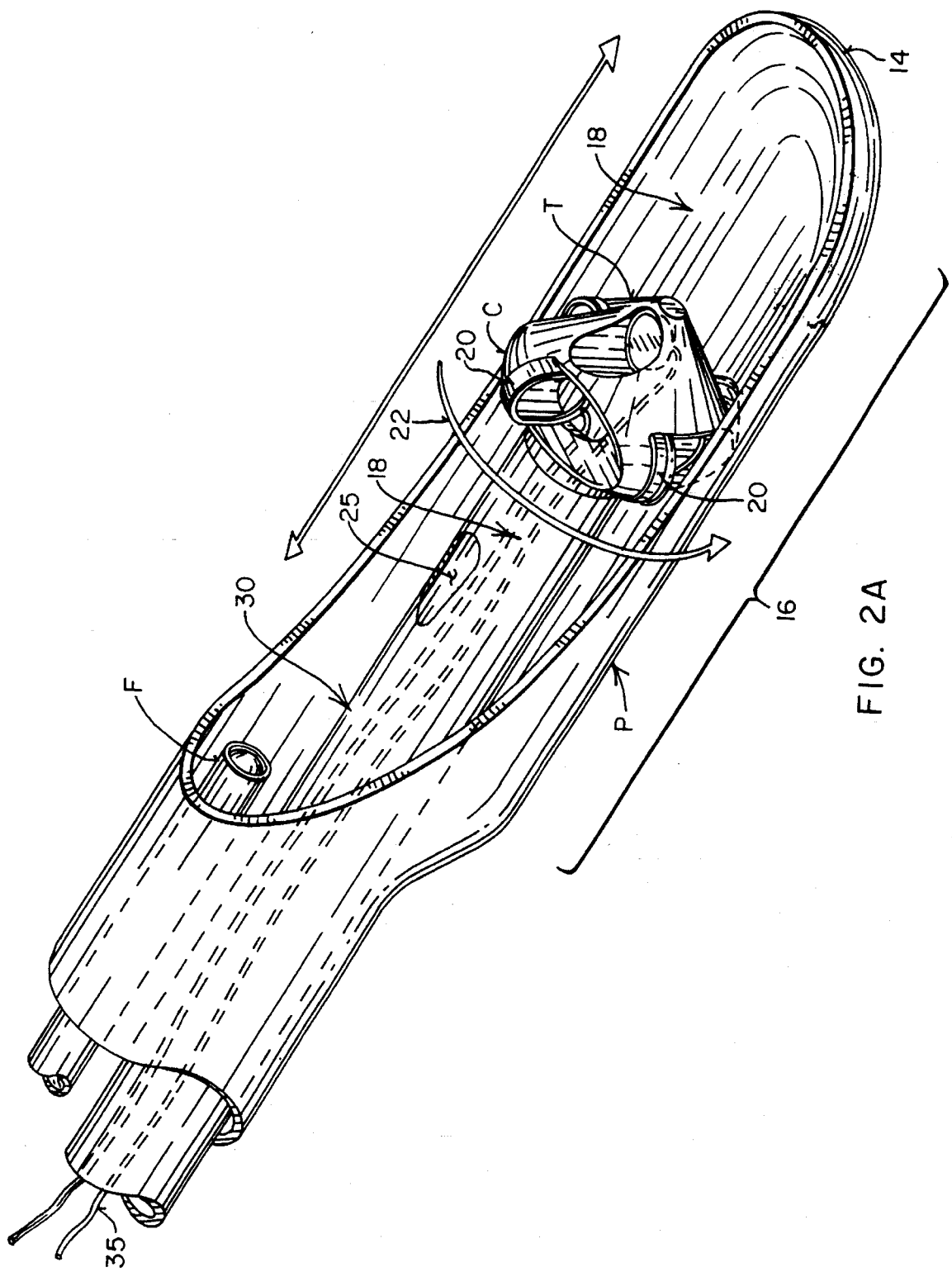
FIG. 2A is a section at the distal end of the probe illustrating the rigid shaft, elongate cutting aperture, infusion lumen, electrocautery cutting head, rotating cutting head driving tube with integral aspiration lumen, viewing optical fiber, and ultrasound transducer.
Figure 2B:
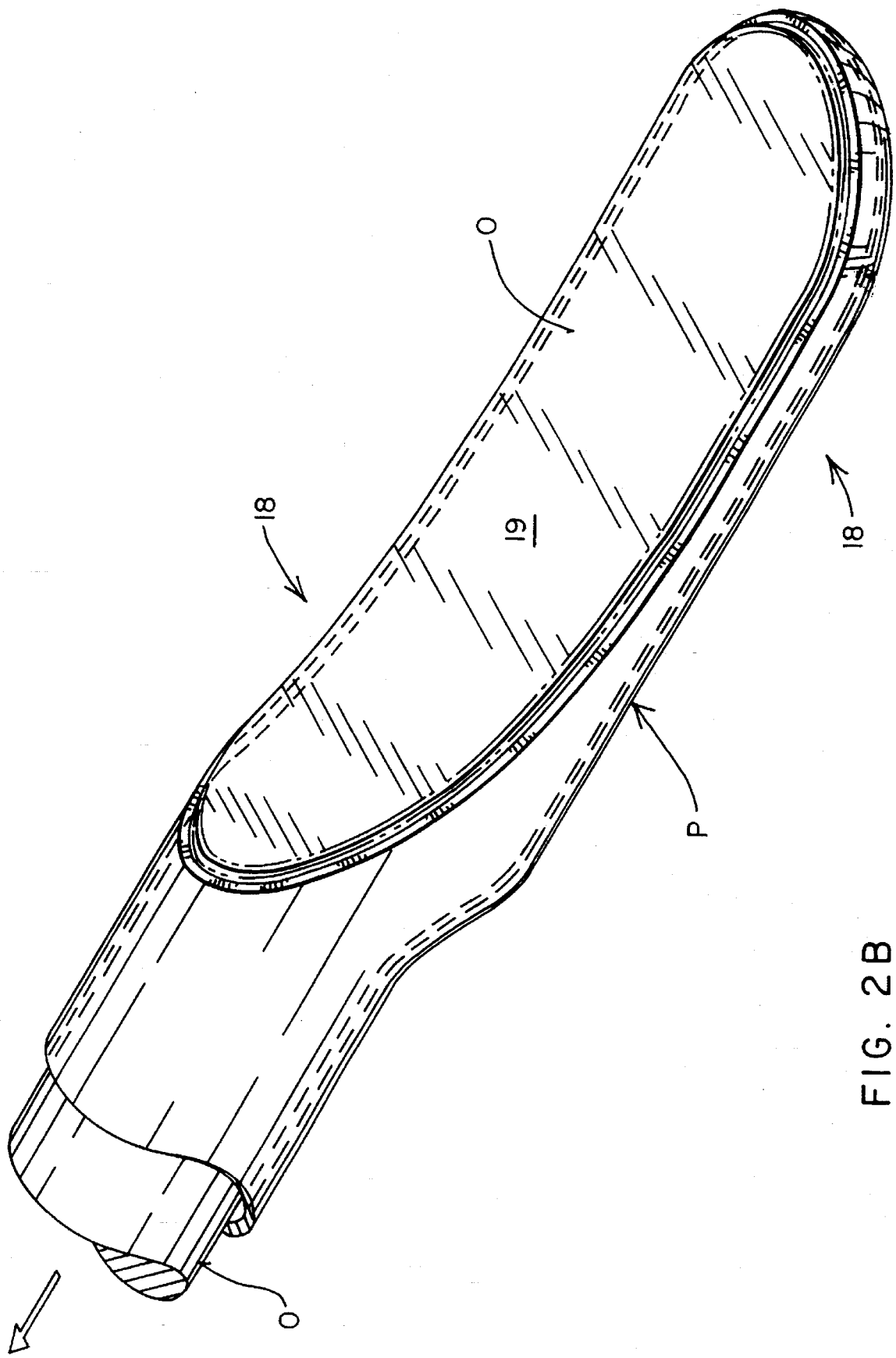
FIG. 2B is a perspective section similar to FIG. 2A with the cutting head removed, and an obturator in place for instrument insertion.

Referring to FIGS. 2A and 2B, probe P is illustrated only at its distal and surgical end. Probe P is rigid having a blunted forward end 14 with an enlarged end 16 for fully accommodating the section of cutting head C. Exposure for surgery of cutting head C occurs at elongate slot 18 with view of the cutting head C during surgery within slot 18 being provided by optical fiber F at the proximal end of the slot. In FIG. 2B, probe P is disclosed occupied by obturator O. It is in this mode that probe P is inserted.

An electrocautery cutting head C is provided. Head C includes electrically conductive cutting edges 20 which are radially exposed from the cutting head C for surgical resection when head C is rotated in the direction of arrow 22. Head C is hollow and communicates to rotating driving tube 30 with interior aspiration lumen 25. An ultrasound transducer T rotates with cutting head C and sends and receives acoustical signals through wire 35. This transducer can measure remaining uterine wall thickness immediately after surgery when head C is in elongate slot 18 drawn proximally or distally of elongate slot 18 or at any intermediate position with respect to the slot.

Cautery alone utilizing probe P can occur. Specifically, by rotating cutting head C opposite to arrow 22, electrocautery cutting heads 20 pass in a blunted and non incisive path over the flesh. Cautery results.

Having generally discussed the construction of the probe, attention can now be directed to handle H.

Referring to FIG. 1A, handle H includes DC motor 40 electrical connections 42—it being recognized that reversal in motor polarity causes reversal in motor direction. Electrocautery connection is routed via a standard cautery power supply through conduit 41 to a journal bearing connection (see FIG. 1A). Acoustical transducer T (seen in FIG. 2A) at cutting head C sends and receives electrical signals through lead 43. A conventional slip coupling—not shown—is provided to wire 35 in tube 30 to lead 43.

Motor 40 is mounted to plate 45 and provides driving rotation at toothed pulley 47. Belt 46 drives toothed pulley 48 which in turn rotates drive tube 30 through quick disconnect coupling 125. This quick disconnect coupling is the point of removable attachment of the probe. (See FIG. 7)

Drive tube 30 is of constant length. Forefinger trigger 50 attaches directly to plate 45 which is mounted for sliding translation interior of handle H. By movement of trigger 50 relative to housing H, corresponding movement of cutting head C occurs along elongate slot 18. Video camera coupler 55 communicates to fiber F having illumination strands for viewing of the applicable surgery.

Referring to FIG. 1A, the fluid circuit for maintaining uterine cavity distention is only illustrated in pertinent part. It is presumed that standard technology will be used to maintain required pressure for uterine cavity distention through inlet conduit 61. Inlet conduit 61 communicates to probe P in the infusion lumen 62. By maintaining a constant pressure sufficient to establish uterine distention, required inflation is maintained in the organ—here the uterus—in which the operation occurs.

Referring to FIG. 7, fluid exits the site of the surgery through lumen 25 in rotating tube 30 and passes to chamber 130 where chips or morsels from surgery are captured. Thereafter, aspirated fluid passes through conduit 65 to finger actuated valve 66 and thence to state of the art fluid capture apparatus. As is customary in such procedures, chips or morsels are routed to pathology for investigation including biopsies where required. The instrument may be shipped intact or be bent (as at shaft 30) for convenience. Disposal can thereafter occur.

Figure 1B:
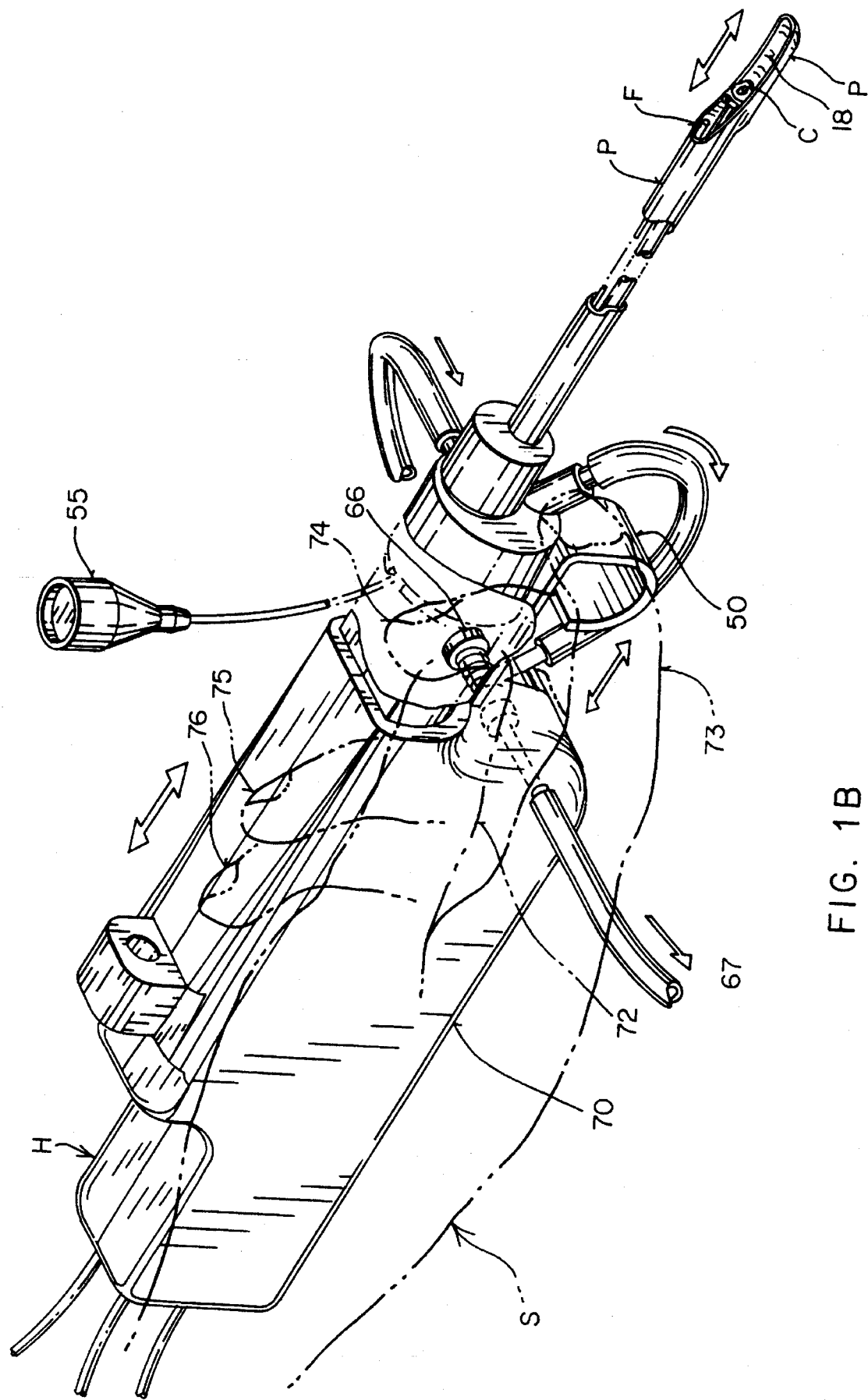
FIG. 1B is a perspective of the drive housing H with probe attached illustrating the housing grasped in the hand of the surgeon (shown in broken lines) demonstrating the surgical instrument manipulation of the rigid probe to dispose the elongate aperture at the surgical site, trigger finger manipulation of the cutting head relative to the viewing fiber and ultrasound transducer, and finger actuated aspiration during surgery.

Referring to FIG. 1B, the surgical ergonomics of housing H can be appreciated. Taking the case of a right handed surgeon, housing H at bottom surface 70 is held by hand S with thumb 72 opposing the third, forth and fifth fingers 74, 75 and 76. Forefinger 73 grips trigger 50 and by movement of finger 73 relative to housing H causes inward and outward traverse of cutting head C relative to elongate slot 18 of probe P. Middle finger 74 depresses valve 66 to cause applicable aspiration for example when view from eyepiece 55 indicates obstruction. Thus, flushing of sorbitol-mannitol solution distending the uterus can occur at intermittent and successive intervals as required by the surgical procedure.

Figure 3A:
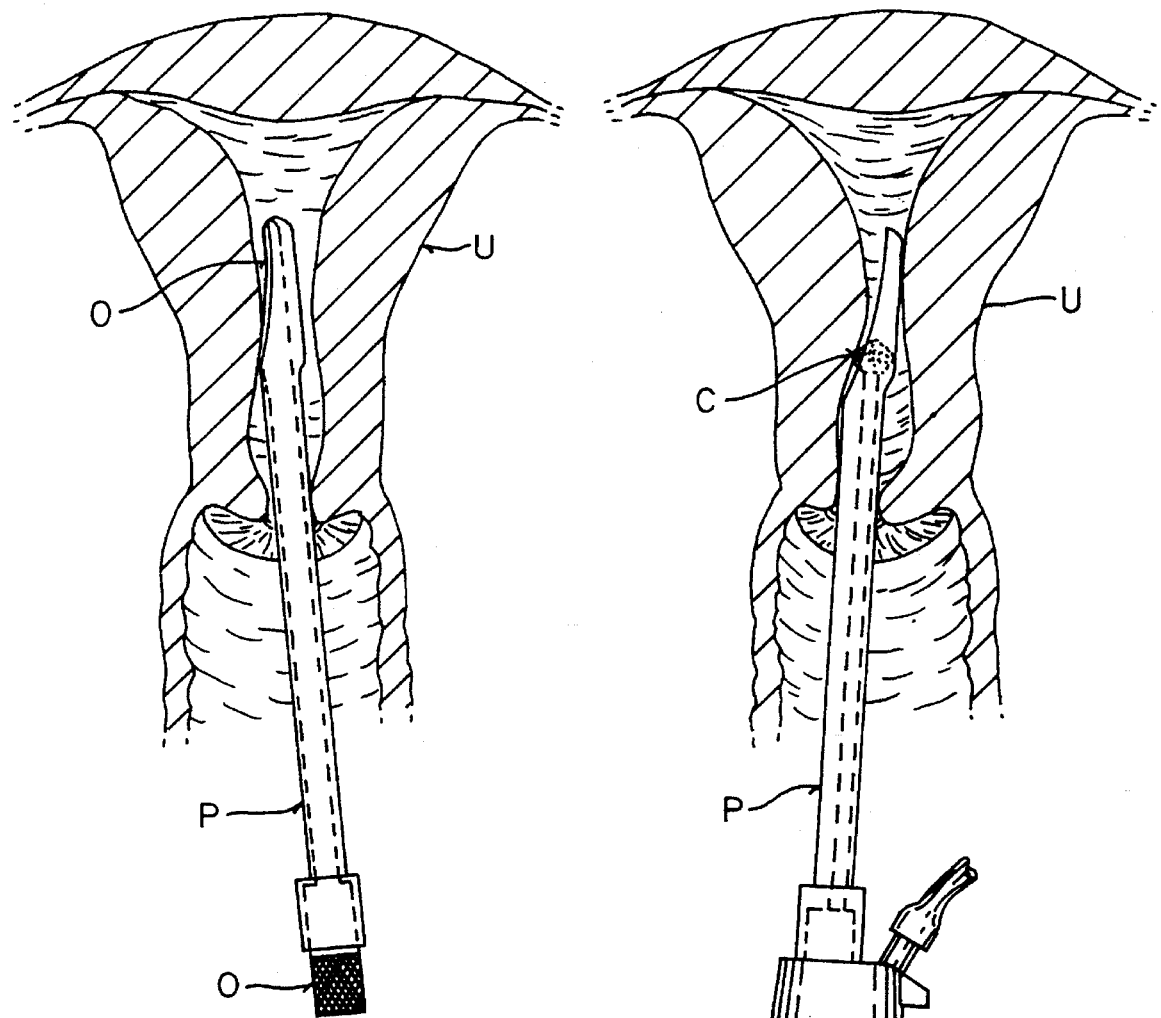
FIGS. 3A, 3B and 3C are respective sections of a uterus respectively illustrating the probe with an obturator during insertion for surgery, the instrument with rotating shaft and cutting head being inserted to the probe; and the insertion of the optical fiber for completion of the assembled probe.
Figure 3B:
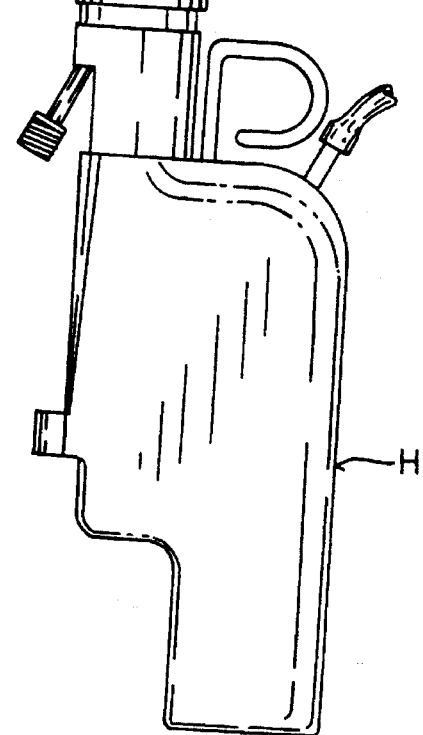
Figure 3C:
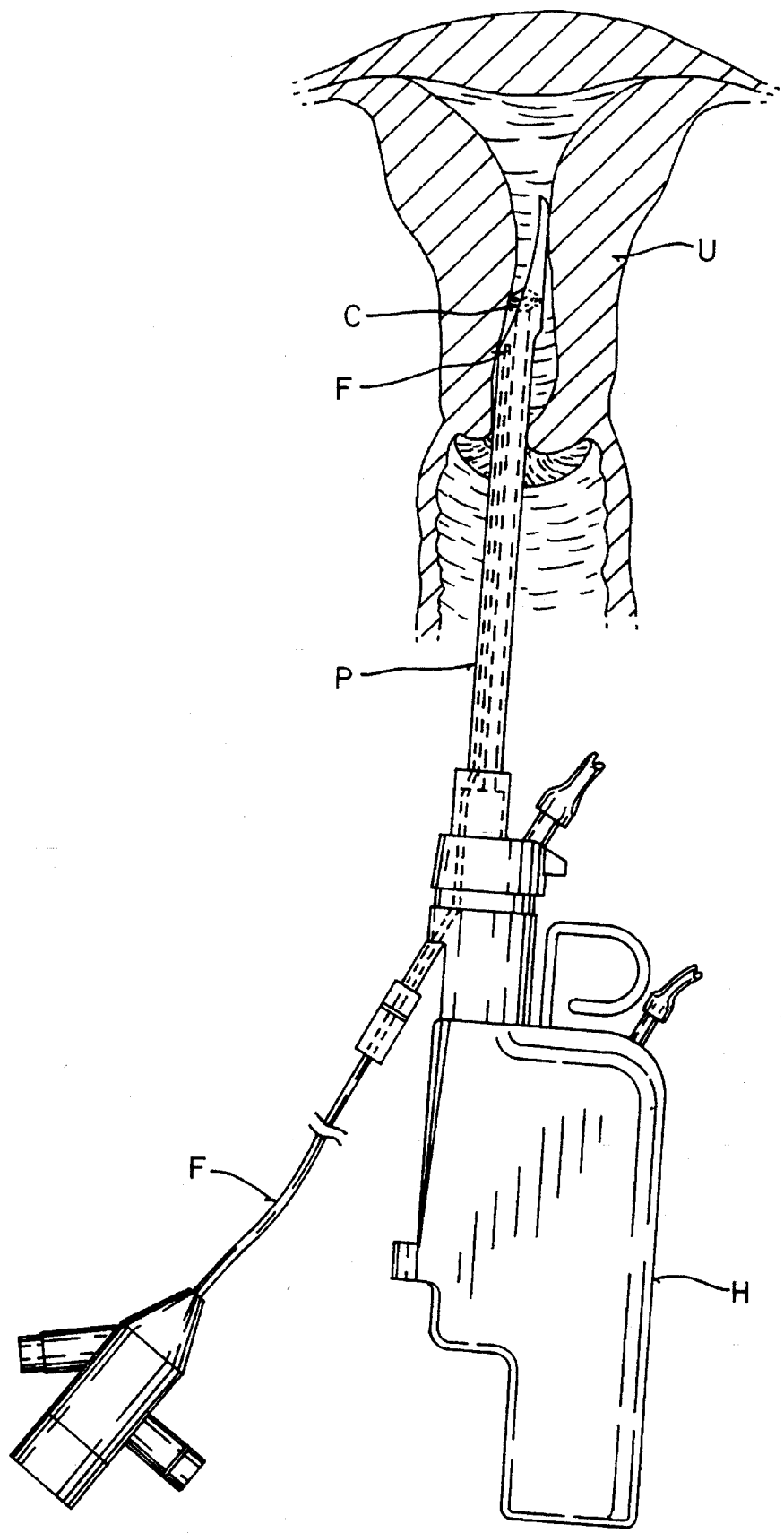

Insert of the instrument is easy to understand. Referring to FIG. 3A, probe P with obturator O is inserted to uterus U. Thereafter, obturator O is withdrawn, and housing H with cutting head C threaded (See FIG. 3B). Once this insertion is made, fiber F is thereafter inserted for visualization of the surgical site (See FIG. 3C and the section of FIG. 8). Operative movement of the instrument can thereafter occur as illustrated in FIG. 4.

Figure 4:
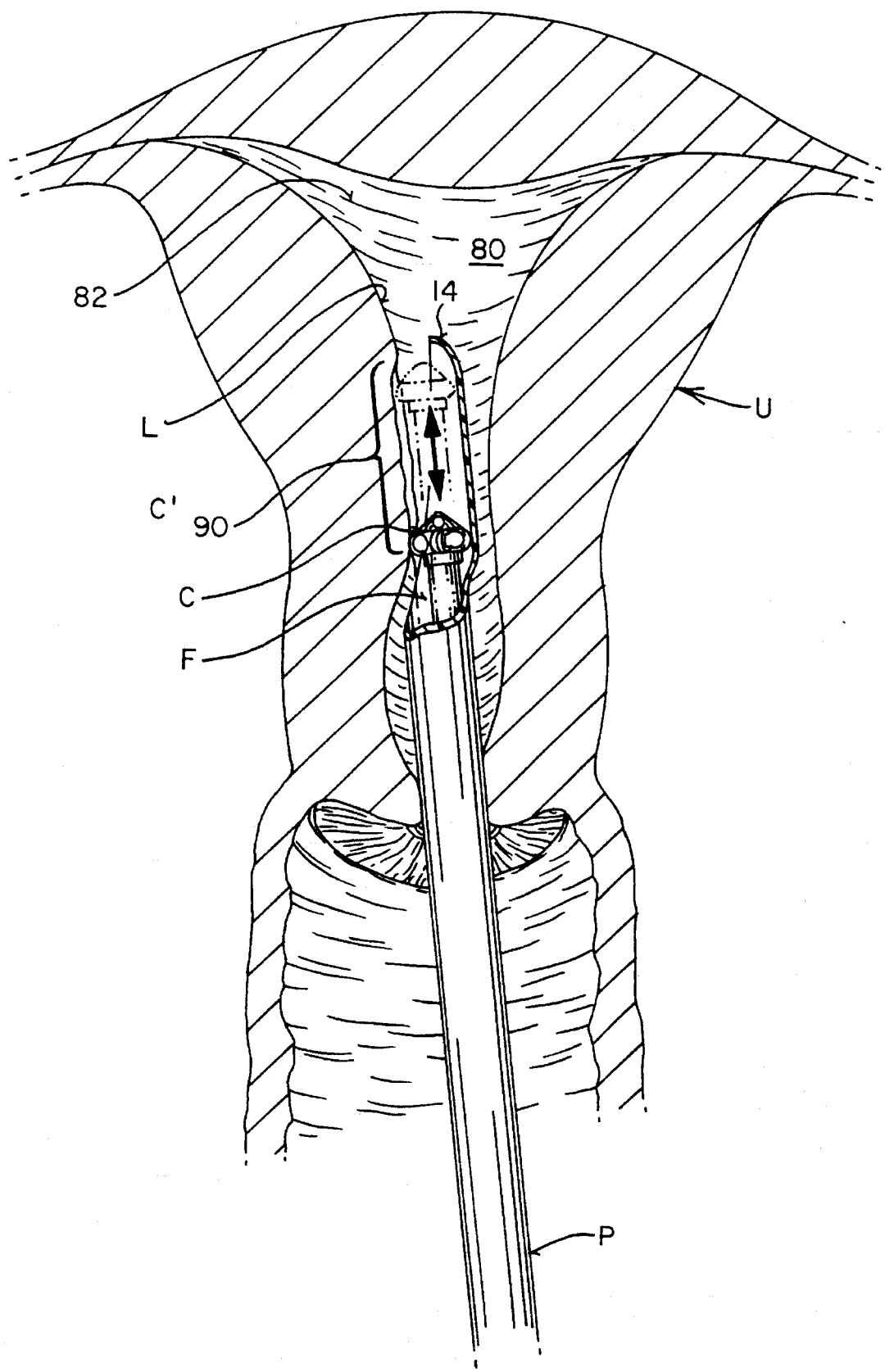
FIG. 4 is a section similar to the sections of FIGS. 3A–3C illustrating the working end of the instrument at an operative site.

The instrument in use can be visualized in the uterine section of FIG. 4. Probe P is shown with blunt end 14 within uterine cavity 80. This cavity is flooded with sorbitol-mannitol solution 82 so as to dispose lining L for surgery. In the preferred method, cutting head C is disposed at C'. Under the guidance of fiber F, probe P is maneuvered to surgical site. Assuming resection, cutter head C is drawn proximally of elongate slot 18 in probe P. With the preferred construction illustrated in FIG. 4, three occurrences follow.

First, and starting with cutting head C distally of elongate slot 18, view of the tissue before resection is provided. Secondly, and with traverse of cutting head C, surgical resection occurs. Thirdly, and immediately in the wake of the required resection, acoustical transducer T interrogates uterus U immediately after the surgery.

It will be remembered that evacuation of fluid occurs directly from the cutting edges of cutting head C to rotating tube 30 with its aspiration lumen 25. Accordingly, flushing of chips and morsels is immediate the surgical site 90 with minimal chance for clouding the required view through fiber F.

Figure 5:
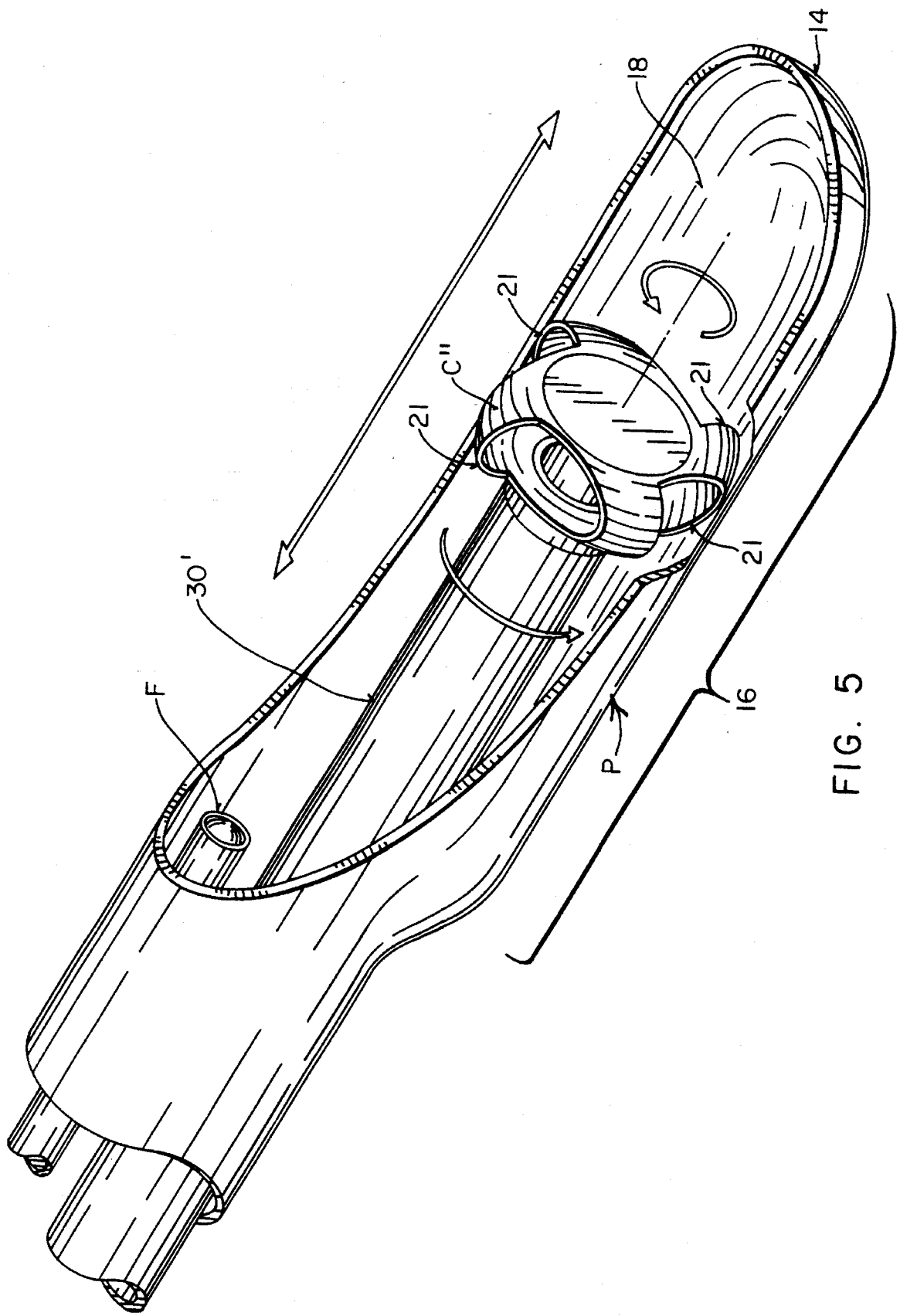
FIG. 5 is a section similar to FIG. 2A of an alternate embodiment of the probe here illustrated with a conventional cutting head without ultrasound interrogation.

Referring to FIG. 5, an alternate embodiment of cutting head C" is illustrated. Cutting head C" is hollow, attached to rotating tube 30', and included semi-spherical cutting edges 21. It will be noted that this head does not include acoustical transducer T nor does it include electrocautery. While both these features are preferred, they are not required.

It is to be understood that acoustical interrogation of uterus U immediately after surgery is not trivial. Specifically, and during the illustrated procedure utilizing operating tools and procedures of the prior art, one of the most difficult assignments of the surgeon is not to cut entirely through the uterus. Such cutting causes morbidity such as iatrogenic uterine perforation and can damage nearby body structures such as bowel.

Fortunately, soft tissue organs such as uterus U can be acoustically interrogated for their remaining wall thickness after resection. Thus transducer T can output through conventional acoustical visualizing apparatus the thickness remaining of the organ. Additionally, and with a conventional shaft encoder, an acoustical section or well known "B" scan of the section at the angle of view of the transducer can be displayed. For example, the remaining width when below a predetermined thickness can be utilized with its telltale acoustical signal to trigger an alarm warning the surgeon when remaining thickness is below a set tolerance.

It will be apparent that the tool of this application will admit of a number of differing cutting heads. For example, as indicated in FIG. 6A, it may be desired to have the cutting head end in a V-shaped cutting profile 101. Further and as set forth in FIG. 6B, and with modification to the probe, a rotating U-shape cutter 102 may be required for distal or end-on access to surgical sites. Finally, and as set forth in FIG. 6C, a flat cutter 103 is shown. It will be realized that this invention will admit of other shapes. Further, the respective cutting heads can either be conventional knives or be provided with suitable paths for electrocautery.

Referring to FIG. 7, the aspiration of fluid from the surgical site together with the trapping of morsels from surgery from the aspirated fluid can be understood. First, perfusion fluid is introduced through conduit 61 into perfusion chamber 100. It then enters probe P.

Viewing FIG. 8 at this juncture can be instructive. Specifically, bearing member 102 with fiber F and rotating tube 30 receiving concavities is placed interior of probe P and extends almost the full length of the lumen within probe P. It includes a lower round aperture 107 which is the surface against which rotating shaft 30 bears. The upper surface forms a saddle which locates and guides the viewing scope F which may be flexible. The remaining interior volume of probe P forms a channel which contains the perfusion fluid. Exit of the fluid occurs through slot 18 and the end of probe P.

Rotating shaft 30 extends completely through chamber 100 and into and through a housing defining chamber 130. Chambers 100 and 130 may be separated by an O-ring (See FIG. 7) or other suitable seal. It is in this housing that the morsels from surgery are trapped. Thereafter, shaft 30 terminates at a quick disconnect coupling 125 which couples to a counter part coupling member 126 driven by motor 40. (See FIG. 1B for this detail).

Interior of chamber 130, shaft 30 is provided with an aperture 128. Aperture 128 allows aspirated fluid to be communicated to chamber 130. Aspirated fluid is withdrawn from chamber 130 through conduit 65. Conduit 65 communicates through valve 66 and outflow conduit 67 for the discharge of aspirated fluid. (See FIG. 1B for valve 6 and conduit 67)

Screen 135 divides chamber 130 between aperture 128 (which rotates with shaft 30) and conduit 65. As a consequence, morsels from surgery are trapped on screen 135. This being the case, the attached probe P when removed from handle H can constitute both a disposable appliance as well as a convenient cartridge 64 for transport of surgical morsels for biopsy. (See FIGS. 1A and 7)

As is apparent, the disposable portion of the device may or may not include probe P.

As a known alternative to the cautery illustrated herein, heated fluids can be flowed through the instrument to coagulate the tissue.

The preferred and illustrated application of this design is for trans-cervical fibroid removal, removal of myometrium, and removal of endometrium. Other uses of instruments substantially incorporating this design are listed below:

Intrauterine (Hysteroscopy)
    Uterine wall Resection
    Endometrial Ablation
    Endometrial Resection
    Submucous Myoma Resection
    Intramural Myoma Resection
    Transmural Myoma Resection
    Resection of Cervix and Cervical Canal Kidney Resection (Laparoscopy)
    Retroperitoneal Prostate Resection (Cystoscopy)

Intra-abdominal (Laparoscopy)
    Uterine Myomectomy
    Ovary Resection

Lung tissue and Tumors (Thoracoscopy)

Measuring Device (Ultrasonic Transducer)
    Uterine Wall Thickness
    Endometrium Thickness
    Prostate Thickness
    Intra uterine measurements
    Urethra thickness The above procedures may require relatively minor modifications of the disclosed device.

Figure 9:
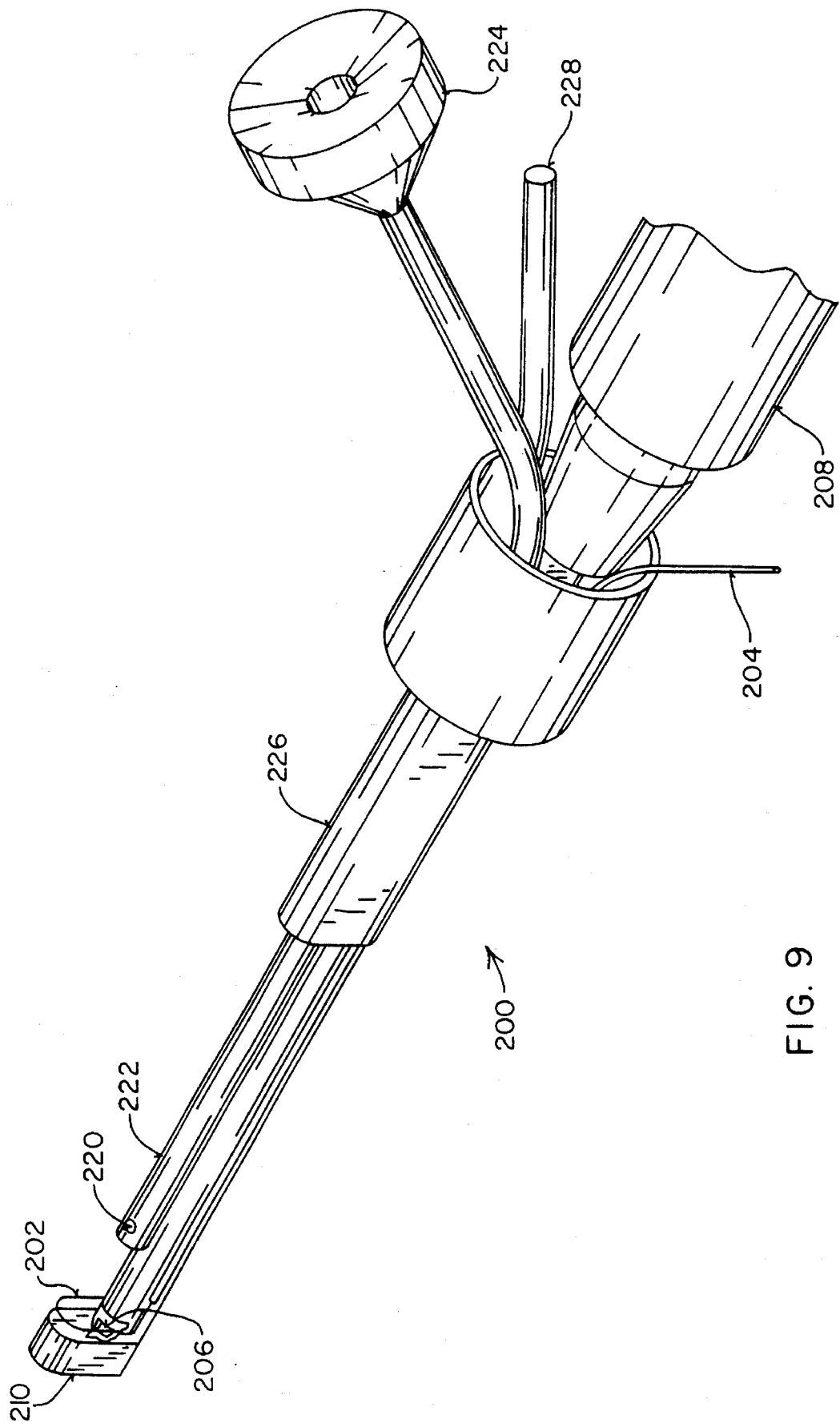
FIG. 9 is a schematic perspective view of an alternative tissue resection device according to the principles of the present invention.

The invention provides an alternative embodiment of a tissue resection/ablation device 200. The device 200 is illustrated schematically in FIG. 9. While the device 200 is particularly advantageous for trans-cervical fibroid removal, removal of myometrium, and removal of endometrium, the device 200 may find other uses including those previously listed above and further including joint arthroscopy. For purposes of convenience, the device 200 will be described with reference to treatment of the uterus. However, the invention is in no way limited to only this type of application.

The device 200 includes an electrosurgical member 202 that is shown schematically in the form of an arch. The electrosurgical member 202 can conveniently be formed from an electrically conductive wire, metal strip, or the like, and can be fashioned in any shape depending on the particular application. Fashioning in the form of an arch is advantageous when removing fibroid tissue from the uterus because strips of tissue can rapidly be removed by translating the electrosurgical member 202 through the tissue. Current is provided to the electrosurgical member 202 through a wire 204 which is in turn connected to an electrosurgical unit.

When electrosurgically removing tissue using prior art methods, the surgical site within the uterus rapidly fills with debris created from the removed tissue. Removal of this debris becomes imperative to allow the surgeon to maintain a clear view of the operation site. Prior art attempts to remove such debris include "sweeping" away the debris between cutting strokes, and periodically removing the electrosurgical device from the uterus to flush or suction away the debris. In the present invention, the removed tissue is immediately evacuated from the uterus by directing the tissue strips from the electrosurgical member 202 and into a chopping or severing mechanism 206. The chopping mechanism 206 in turn rapidly reduces the size of the tissue strips so that the tissue can be suctioned through the device 200 and removed from the uterus. In this way, tissue removed by the electrosurgical member 202 is evacuated from the surgical site as rapidly as the surgeon can cut the tissue. The amount of debris created in the uterus is drastically reduced, and the time consuming steps of "sweeping" away tissue or removing the electrosurgical device from the uterus for flushing or suction is eliminated.

The tough and gristly nature of fibroid tissue makes it difficult to remove from the uterus with conventional knife-edged instruments. Use of the electrosurgical member 202 has proven to be effective in such removal. However, once removed by the electrosurgical member 202, the fibroid tissue becomes easier to process, and a conventional arthroscopic cutter can be employed to chop or sever the tissue into smaller morsels. Suitable arthroscopic cutters are described in U.S. Pat. Nos. 4,274,414 and 4,203,444, the disclosures of which are herein incorporated by reference. Briefly, such cutters include a rotating concentric tube having a shaving port into which the tissue is directed. The rotating blade chops the fibroid tissue into small transportable morsels or chips which can then be removed from the uterus through the concentric tube by suction. Although such cutters are preferred, a variety of different chopping mechanisms can be employed including reciprocating blades, grinders, and the like, a necessary requirement being that the mechanisms chop, sever or reduce the tissue into smaller morsels for evacuation. A motor 208 is provided to rotate the chopping mechanism 206. The motor 208 further includes a vacuum valve and an associated vacuum port for providing suction to remove the chopped tissue from the uterus.

To assist in directing the strips of tissue removed by the electrosurgical member 202 towards the chopping mechanism 206, an end cap 210 is provided just distal to the electrosurgical wire 202. In this way, tissue removed when translating the electrosurgical member 202 is directed by the end cap 210 into the chopping mechanism 206. The chopping mechanism 206 in turn chops the tissue as it is fed from the end cap 210 so that substantially all tissue removed by the electrosurgical member 202 is chopped and removed from the uterus. Operation of suction and motor 208 without electrocautery allows the device 200 to extract loose floating debris that may have escaped the initial cutting/extraction process.

Visualization of the surgical site while removing tissue can be provided by an ultrasonic transducer 220 disposed near the electrosurgical member 202. The ultrasonic transducer 220 provides information on the thickness of the uterine wall where the fibroid material is being removed. By monitoring uterine wall thickness in this way, removal of fibroid material can be halted before perforating and damaging adjacent structures such as the bowel or bladder. The ultrasonic transducer determines wall thickness as previously described with transducer T. Briefly, a pulse signal is sent through the uterine wall and the time required to receive a return pulse is measured. Based on this measurement, the thickness of the uterine wall can be calculated. This information can be viewed on a conventional oscilloscope screen, or the thickness can be displayed numerically. To map the area of the uterine wall near the area where the desired cut is to be made, a plurality of such measurements are made. Based on this information, the surgeon can estimate the appropriate depth for the entire length of the cut. Instead of displaying the result of each individual measurement on a oscilloscope screen or displaying a numeric value, a "B" scan can be made and entered into a processor to produce a visual image of the uterine wall. The visual image can then be evaluated to determine the appropriate depth for the cut.

The ultrasonic transducer 220 can be used independently of the electrosurgical member 202, e.g., by removing the electrosurgical member 202 or by not actuating it, as a diagnostic tool. When used as a diagnostic device, the transducer 220 is used to map the a body organ from within the organ. For example, the transducer can be positioned within the endometrial cavity of the uterus and actuated to map the endometrial cavity and the uterine wall. In this way, abnormalities in the uterus can be diagnosed.

Visualization of the surgical site during operation of the electrosurgical member 202 can also be provided by a fiber optic scope 222 near the electrosurgical member 202. The fiber optic scope 222 provides conventional visual feedback through an eyepiece 224 to which a video camera is commonly coupled for display on a video monitor and for creating a tape record of the procedure. The fiber optic scope 222 and the ultrasonic transducer 220 can be used separately or can be used together to provide both conventional optical visualization and ultrasonic visualization of uterine wall thickness.

The tissue resection device 200 will usually be introduced into the cervix through a sheath 226. To facilitate introduction of the sheath 226, an obturator is usually first inserted into the sheath 226. Once the sheath 226 is inserted into the uterus, the obturator is removed from the sheath 226 and the device 200 is inserted into the sheath 226. The sheath 226 provides a working channel through which the electrosurgical member 202, the chopping mechanism 206, the fiber optic scope 222, the ultrasonic transducer 220, and other components of the device 200 can be inserted. When the components of the device 200 are introduced into the sheath 226, a seal is formed between the components of the device 200 and the sheath 226 (see FIG. 10). In this way, irrigation fluid can be applied through an irrigation tube 228 to distend the uterus before tissue removal, and to make up for fluid used in the extraction process.

Figure 10:
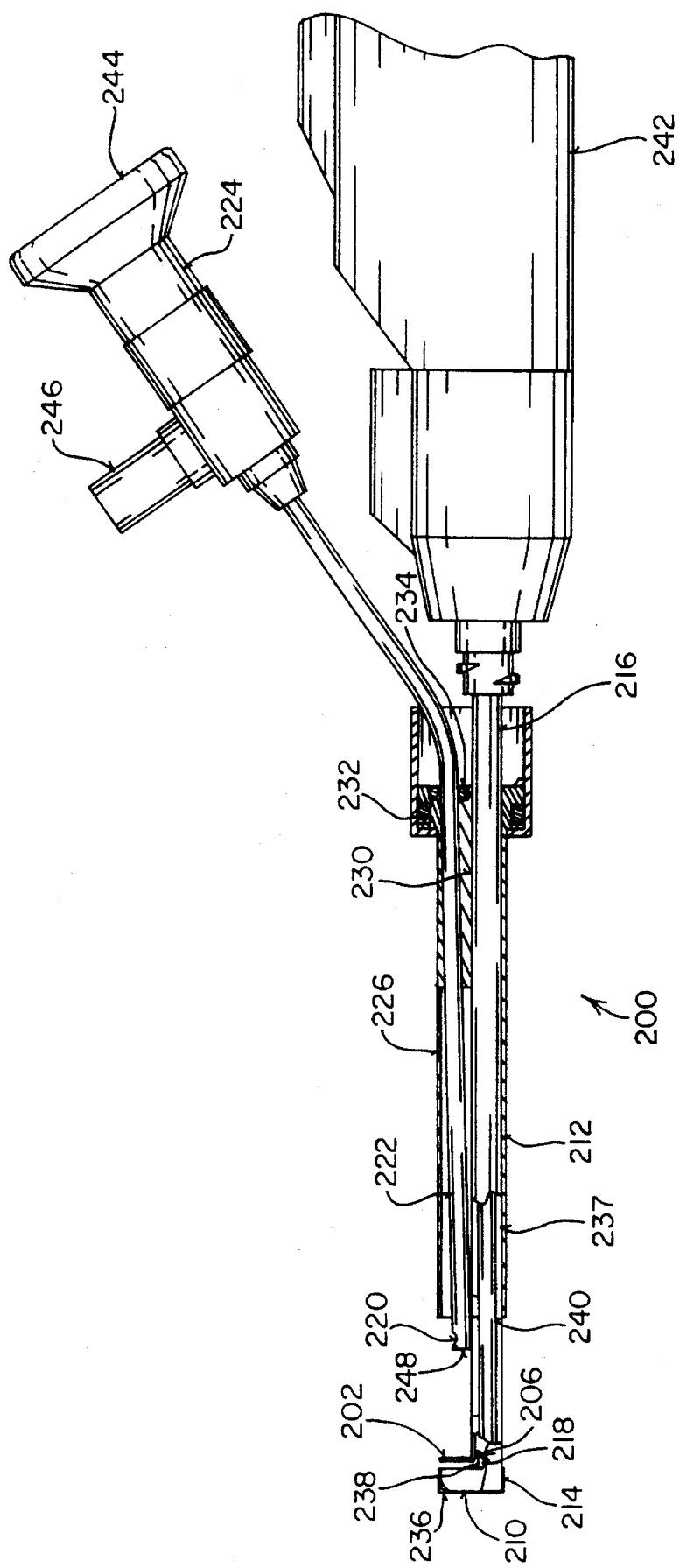
FIG. 10 is a detailed cut-away side view of an exemplary tissue resection device patterned according to the schematic of FIG. 9.

Referring to FIG. 10, an exemplary embodiment of a tissue resection device will be described. The device of FIG. 10 is patterned after the schematic of FIG. 9. For purposes of convenience, the embodiment shown in FIG. 10 will use the same reference numerals as used to schematically describe the tissue resection device 200 in FIG. 9. The device 200 includes an elongate body 212 having a distal end 214 and a proximal end 216. The elongate body 212 houses the chopping mechanism 206 and holds the electrosurgical member 202 in a fixed position relative to the chopping mechanism 206. To position the elongate body 212 and the fiber optic scope 222 within the sheath 226 (shown cut away to illustrate positioning of the components), a guide 230 is provided within the sheath 226. (For purposes of clarity, the irrigation lumen 228 and wire 204, which pass through channels in the guide 230, have been omitted.) The guide 230 is slidable within the sheath 226 and also provides a seal between the components and the sheath 226 so that distention pressure can be maintained inside of the uterus during operation. The guide 230 is preferably constructed of plastic, but can alternatively be constructed of a variety of other materials including stainless steel, brass, aluminum, and the like. The guide 230 is preferably permanently fixed to the outside of the elongate member 212 and includes O-rings 232 and 234 for sealing the guide 230 to the sheath 226 and scope 222. The sheath 226 will be preferably constructed of stainless steel which can be sterilized and reused.

The electrosurgical member 202 will preferably comprise an electrosurgical wire that is formed into a loop, an arch, or other suitable geometry. The electrosurgical wire 202 is attached to the outside of the elongate body 212 and is positioned above an aperture 218 in the elongate body 212 which provides access to the chopping mechanism 206. The end cap 210 is fixed to the distal end 214 of the elongate body 212 so that strips of tissue removed by the electrosurgical wire 202 are directed by the end cap 210 into the aperture 218.

An electrically conductive area 236 (or plurality of areas) is provided on the outside surface of the end cap 210 that can be connected to the same electrosurgical unit used to provide current to the electrosurgical wire 202. When actuated, the electrically conductive area 236 can be applied to bleeding tissue to promote coagulation to stop bleeding or can be used for endometrial ablation. When used for ablation, the end cap 210 will preferably be constructed of a ceramic, and the electrically conductive area 236 will preferably be a metallic surface on the cap 210 that is connected by a separate wire to the electrosurgical unit.

Figure 10A:
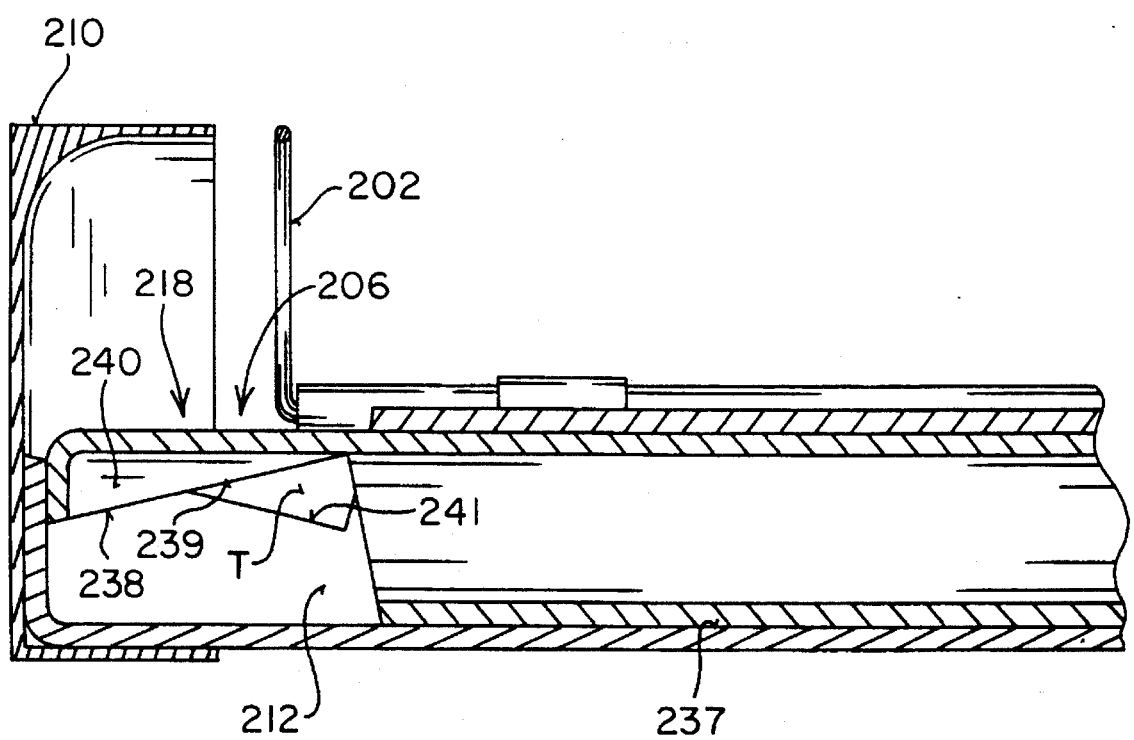
FIG. 10A is an enlarged cross-sectional view of the distal end of the tissue resection device of FIG. 10.

The elongate body 212 includes a central lumen 237 extending between the distal end 214 and proximal end 216. Held within the lumen 237 is the chopping mechanism 206. As shown best in FIG. 10A, the chopping mechanism 206 will preferably include a concentric rotating tube 240 disposed within the lumen 237. A shaving port 238 is formed in the wall of the tube 240 and is generally aligned with the aperture 218 of the elongate body 212. An edge 239 of the shaving port 238 and an edge 241 of the aperture 218 are sharpened so that any tissue drawn through the aperture 218 and shaving port 238 are sheared upon rotation of the concentric tube 240. In FIG. 10A, the rotating tube 240 is shown with the shaving port 238 facing away from the aperture 18. The triangle area TR is an opening between the edges 239 and 241. As the tube 240 is rotated, the edge 239 of the shaving port 238 is translated across the edge 241 of the aperture 218 until the triangle area TR disappears. Any tissue extending through both the shaving port 238 and the aperture 218 is sheared by the edges 239 and 241. Upon each revolution of the tube 240, another morsel of tissue is sheared.

The concentric tube 240 is rotated by the motor 208 (not shown) held within a housing 242. The housing 242 includes vacuum ports for connection to a house vacuum and associated vacuum valves for regulating suction. The suction is applied through the tube 240 thereby allowing the chopped morsels to be evacuating from the uterus.

In an alternative embodiment, the electrosurgical wire 202 can be slidably mounted on the elongate body 212, and a trigger mechanism can be used to axially translate the wire 202 in a smooth and controlled manner along the body 212. In this way, the wire 202 is translated relative to the scope 222.

The eyepiece 224 includes a viewing element 244 and an illumination connector 246. When the illumination connector 246 is attached to a suitable light source, light is provided to the optical fiber within the scope 222. This allows a surgeon to look through the viewing element 244 and visualize the operation site near the electrosurgical member 202. The ultrasonic transducer 220 is disposed on top of the optical scope 222 and is positioned so that its field of view includes the operative area above the electrosurgical wire 202. In this manner, the operative area where tissue is being removed by the electrosurgical wire 202 can be optically viewed by the scope 222 and the wall thickness can ultrasonically be visualized by the transducer 220. The optical scope 222 is slidably held within the guide 230 so that scope 222 can be axially translated to adjust the viewing area of both the scope 222 and the ultrasonic transducer 220. In an alternative embodiment, the ultrasonic transducer 220 can be provided on a separate instrument that is inserted parallel to the scope.

Figures 11, 11A:
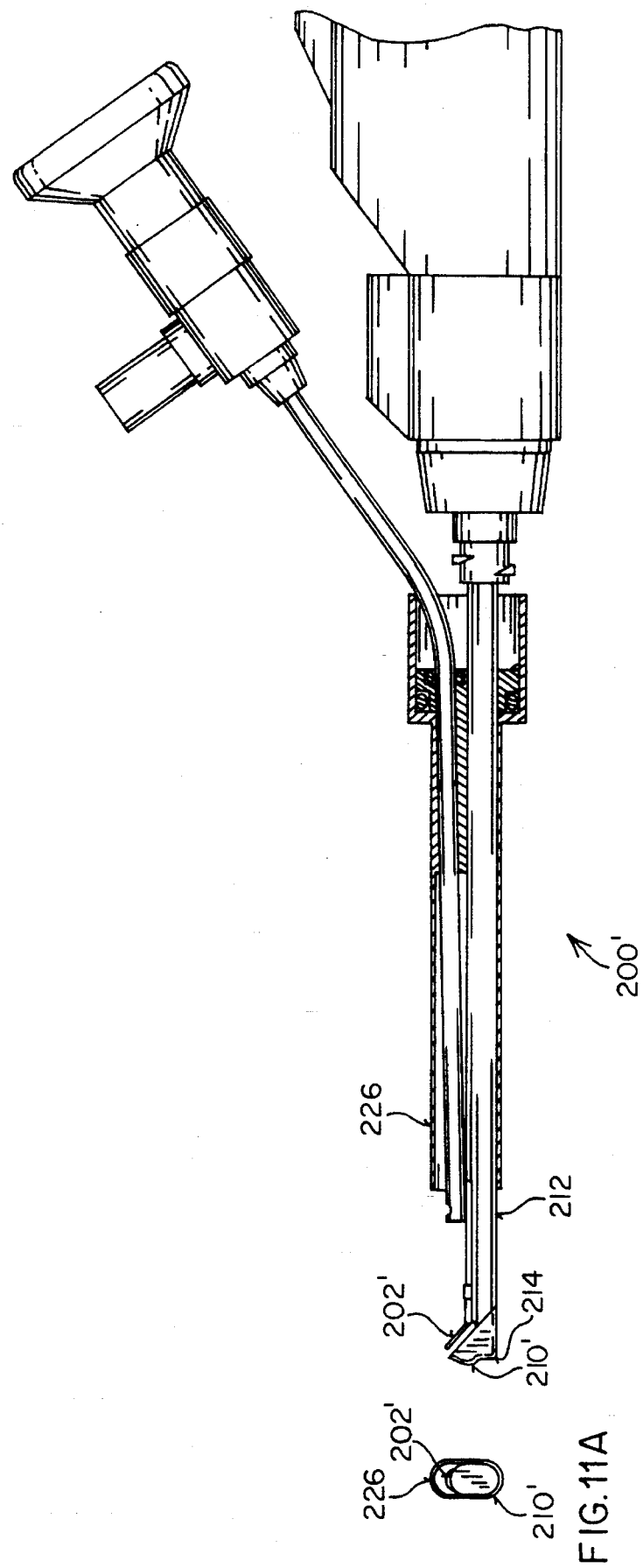
FIG. 11 is a detailed side view of an alternative embodiment of the device of FIG. 10 with an angled electrocautery loop.
FIG. 11A is a front end view of the device of FIG. 11.

An important feature of the resection device 200 is that a variety of electrosurgical wire/end cap/chopper configurations can be employed to provide greater flexibility and effectiveness in treatments. One such alternative embodiment is the tissue resection device 200' shown in FIGS. 11 and 11A. The tissue resection device 200' is essentially identical to the tissue resection device 200 except for the end cap and the positioning of the electrosurgical wire. In the resection device 200' an electrosurgical wire loop 202' is angled toward the distal end 214 of the elongate body 212, preferably at any angle relative to the elongate body 212. Alternatively, the loop 202' can be angled away from the distal end 214 at any angle. Angling of the wire 202' toward the distal end 214 is advantageous when treating difficult to reach areas such as the top of the uterus. An end cap 210' is correspondingly angled so that the end cap 210' does not interfere with the cutting performance of the wire 202'. As with the previous embodiment, the end cap 210' serves as a director for directing tissue into the chopping mechanism 206.

Referring to FIGS. 12 and 12A, a further embodiment 200" of the tissue resection device 200 will be described. The resection device 200" is essentially identical to the tissue resection device 200' described in FIG. 11 except for the configuration of the end cap 210'. In the tissue resection device 200", an end wire 250 is provided at the distal end 214 of the elongate body 212. Use of the end wire 250 is advantageous in that it allows an optical viewing path for the optical scope 222 beyond the distal end 214 of the device 200". This allows for viewing of the area where the device 200" is being positioned in preparation for a cut. FIG. 12A represents a view from the distal end 248 of device 200". Although the view is partially blocked by the end wire 250 and the electrosurgical wire 202, sufficient space is provided between the wires so that a surgeon can view beyond the distal end 214 when looking through the eyepiece 224. A shell 252 is welded or bonded to the elongate body 212. Along with the end wire 250, the shell 252 serves to direct removed tissue into the chopping mechanism 206. The shell 252 can optionally be provided with electrically conductive areas which can be used to cauterize or thermally ablate tissue as previously described.

As shown in FIG. 12, the ultrasonic transducer 220 is included on the optical scope 222. Alternatively, as shown in FIGS. 13 and 13A, ultrasonic transducer 220 can be held in a shaft 260 separate from the optical scope 222. In such a configuration, the optical scope 222 will preferably be a 2 mm optical scope that is aligned with an aperture 256 in the end wire 250 so that optical visualization can occur beyond the distal end 214. Both the shaft 260 and the scope 222 are slidable within the sheath to allow the optical scope 222 and the ultrasonic transducer 220 to be adjusted independently of one another.

Figure 14:
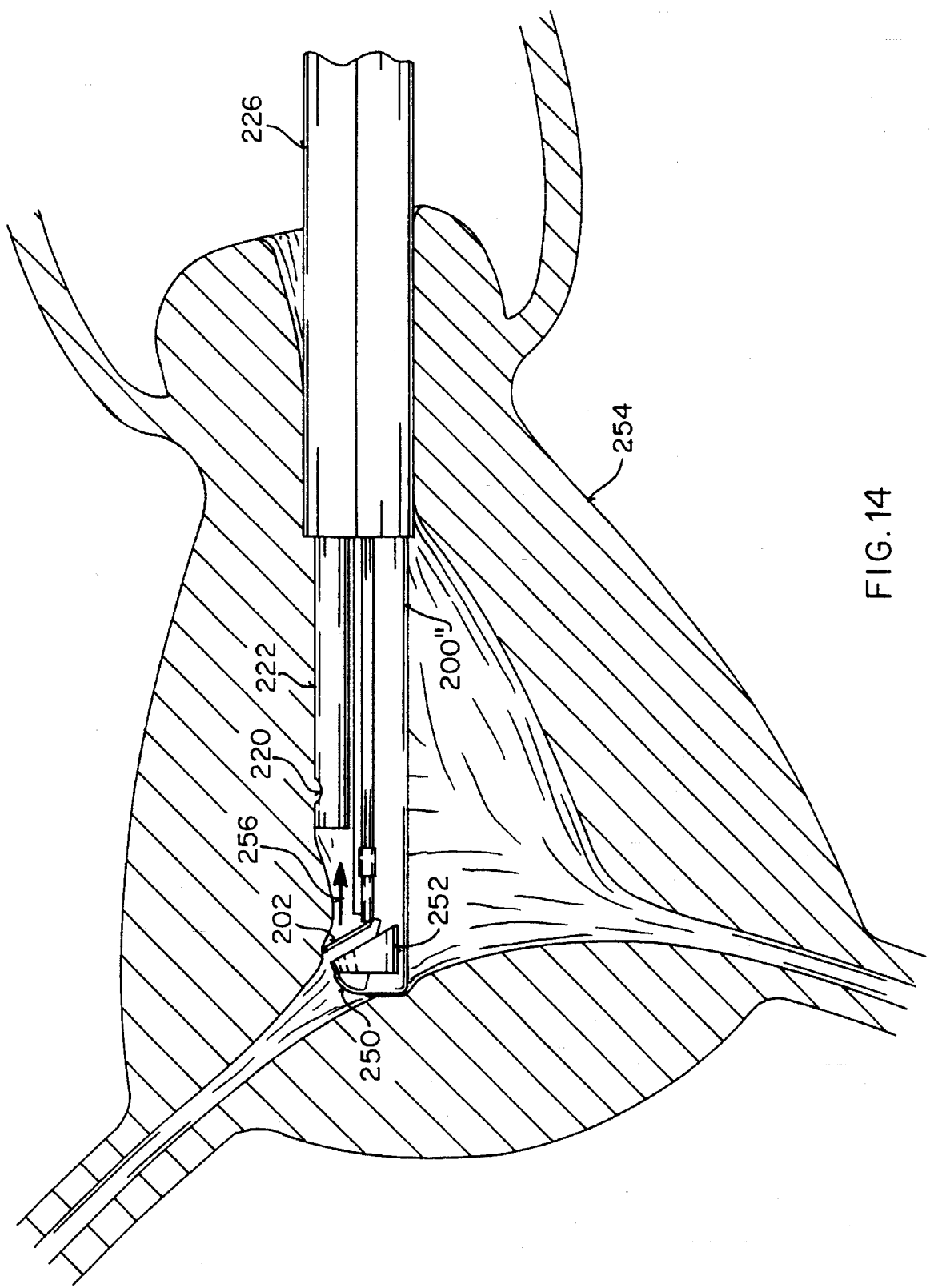
FIG. 14 illustrates an exemplary method for resecting tissue from the uterus using the device of FIG. 12.

Referring to FIG. 14, an exemplary method for using the tissue resection device 200" will be described. Although described in the context of the device 200" for convenience, the method can also be used with the previously described embodiments of the tissue resection device 200 and 200'. Initially, the sheath 226 is inserted into the uterus using an obturator (not shown) as previously described. The obturator is then removed and the device 200" is inserted into the sheath 226. Once a seal is formed between the sheath 226 and the guide 230, fluid is introduced into the uterus 254 for distention. While optically and/or ultrasonically viewing the uterus 254 with the fiber optic scope 222 and/or the ultrasonic transducer 220, current is delivered to the electrosurgical wire 202 and the wire 202 is translated along the lining of the uterus 254 as indicated by arrow 256. Alternatively, before commencing a cut, the ultrasonic transducer 220 can be actuated to survey and map the thickness of the uterus in the desired treatment area.

The wire 202 is translated by sliding the device 200" within the sheath 226. As the wire 202 is translated, strips of tissue are removed and directed to the chopping mechanism 206 by the end wire 250 and shell 252. The removed strips of tissue are then chopped into smaller morsels by the chopping mechanism 206 as previously described. After the completion of the first cut, the surgeon directs the electrosurgical wire 202 to an adjacent area and draws the wire through the fibroid. With the completion of each cut, the wire 202 is repositioned and another cut is begun. The amount of material removed is controlled by the manually maneuvering, e.g., lifting or pivoting, the device 200" to adjust the depth of penetration of the wire 202 into the uterus and by the length of the cutting stroke.

In this way, strips of removed tissue are automatically directed into the chopping mechanism 206 for removal from the uterus. This reduces the time and effort normally incurred in removing shavings which block the field of view of the surgeon. Further, since the device does not need to be withdrawn from the uterus 254 to remove the shavings, the task of reorienting the device 200" is eliminated. Fatigue is also reduced which allows the surgeon to perform more precise work.

Although the foregoing invention has been described in detail by way of illustration and example, for purposes of clarity of understanding, it will be obvious that certain changes and modifications may be practiced within the scope of the appended claims.

What is claimed is:

1. A method for resecting prostatic tissue, said method comprising:

providing a probe defining a lumen and having a distal end open at an elongate slot;

providing a rotatable cutting head having laterally disposed cutting edges relative to an axis along the lumen of the probe, the cutting head having a dimension sufficient to fit into and through said lumen of said probe, said cutting head having means for directing tissue resected by said cutting edges into said lumen;

providing a tube attached to said rotatable cutting head so that said cutting head is disposed at said elongate aperture;

inserting said probe within a urethra with said elongate slot confronted to a surgical site;

rotating the tube to rotate said cutting head in contact with prostatic tissue to be resected;

perfusing the surgical site with perfusion fluid and aspirating the surgical site through said lumen to draw resected prostatic tissue from said surgical site; and applying radio frequency energy to the cutting head as it is rotated at a frequency selected to enhance cutting.

2. A method as in claim 1, including the step of applying radio frequency energy to the cutting head at a frequency selected to enhance coagulation.

3. A method as in claim 1, including the steps of reversing the rotation of the cutting head while the radio frequency energy is applied to cauterize with said cutting head.

4. A method as in claim 1, further comprising optically viewing the prostatic tissue to be resected while contacting with the cutting head.

5. A method as in claim 1, further comprising providing a sound transducer on said cutting head; and, ultrasonically viewing the prostatic tissue through said sound transducer to determine depth of prostatic tissue to be resected.

6. A method as in claim 1, further comprising the steps of:

aspirating a perfusion fluid from said surgical site through a tube attached to said cutting head.

7. A method as in claim 1, including the steps of:

perfusing said surgical site through said probe.

8. A method of inserting for surgery a resectoscope for operating on prostatic tissue at a surgical site in a perfused urethra of a human comprising the steps of:

providing a probe having a distal and proximal end and defining a lumen therebetween, said distal end of said probe including an elongate slot adjacent a blunt end;

providing an obturator for occupying said probe at said slot for enabling insertion of said probe to said urethra in said human;

placing said obturator in said probe from said proximal end to occupy said elongate slot and inserting said probe to said urethra in said human body;

withdrawing said obturator from said probe through the proximal end of said inserted probe;

perfusing said urethra with fluid through said lumen in said probe;

providing a rotatable member having a cutting head mounted on the distal end thereof and a proximal end adapted to be rotated, said cutting head and rotating member having a dimension less than the lumen of said probe;

inserting said cutting head and said rotating member to said lumen at said proximal end of said probe to protrude said cutting head from said probe at said slot at said distal end of said probe;

providing an optical fiber for visualizing said cutting head;

inserting said fiber along said lumen to visualize said cutting head in said probe at said slot at said distal end of said probe; and, rotating said cutting head from said rotatable member at the distal end of said probe during said visualization for operating at said surgical site.

9. A method of inserting for surgery a resectoscope according to claim 8 further comprising:

providing a lumen in said rotatable member between the distal end of said member adjacent said cutting head and the proximal end of said member; and, aspirating said perfused surgical site through said lumen in said rotatable member.

10. A method of inserting for surgery a resectoscope according to claim 8 further comprising:

perfusing said cavity with a substantially non-conductive fluid;

providing an electrical path in said rotatable member to said cutting head; and, supplying electrical energy sufficient for cautery to said cutting head.

11. A method of inserting for surgery a resectoscope according to claim 8 and further including:

providing an acoustical transducer in said cutting head having sufficient dimension to fit within said lumen of said probe from said proximal end to said distal end; and, sending and receiving sound at said acoustical transducer during said rotation of said cutting head for acoustical examination of said surgical site.

12. A method for resecting prostatic tissue from the urethra, the method comprising:

removing prostatic tissue from the urethra by applying a cutter or radio frequency to the prostatic tissue;

viewing depth of tissue resection in the urethra while removing the prostatic tissue; and evacuating the removed prostatic tissue from the urethra.

13. A method for resecting prostatic tissue, said method comprising:

providing a probe defining a lumen and having a distal end open at an elongate slot;

providing a rotatable cutting head having laterally disposed cutting edges relative to an axis along the lumen of the probe, the cutting head having a dimension sufficient to fit into and through said lumen of said probe, said cutting head having means for directing tissue resected by said cutting edges into said lumen;

providing a tube attached to said rotatable cutting head so that said cutting head is disposed at said elongate aperture;

inserting said probe within a urethra with said elongate slot confronted to a surgical site;

rotating the tube to rotate said cutting head in contact with prostatic tissue to be resected;

perfusing the surgical site with perfusion fluid and aspirating the surgical site through said lumen to draw resected tissue from said surgical site; and applying radio frequency energy to the cutting head at a frequency selected to enhance coagulation.

14. A method for resecting prostatic tissue, said method comprising:

providing a probe defining a lumen and having a distal end open at an elongate slot;

providing a rotatable cutting head having laterally disposed cutting edges relative to an axis along the lumen of the probe, the cutting head having a dimension sufficient to fit into and through said lumen of said probe, said cutting head having means for directing tissue resected by said cutting edges into said lumen;

providing a tube attached to said rotatable cutting head so that said cutting head is disposed at said elongate aperture;

inserting said probe within a urethra with said elongate slot confronted to a surgical site;

rotating the tube to rotate said cutting head in contact with prostatic tissue to be resected;

perfusing the surgical site with perfusion fluid and aspirating the surgical site through said lumen to draw resected tissue from said surgical site; and optically viewing the tissue to be resected while contacting with the cutting head.

15. A method as in claim 12, wherein the removing step comprises translating a cutting member through prostatic tissue to form a strip of tissue.

16. A method as in claim 15, wherein the evacuating step comprises chopping the strip of tissue into morsels and aspirating the morsels from the urethra.

17. A method as in claim 16, wherein the cutting member is translated longitudinally within the urethra.

18. A method as in claim 17, wherein the chopping step comprises rotating a cutting head having a laterally disposed cutting edge.

19. A method for resecting prostatic tissue from the urethra, the method comprising:

removing prostatic tissue from the urethra by longitudinally translating an electrosurgical cutting member through the prostatic tissue to form a strip of tissue, the cutting member being disposed on a probe;

monitoring depth of tissue resection from the probe while removing the prostatic tissue; and evacuating the removed prostatic tissue by rotating a cutting head of the probe to chop the strip of tissue into morsels and aspirating the morsels from the urethra through a lumen of the probe.

20. A method as in claim 19, further comprising directing the strips of tissue toward the cutting head with an at least partially electrically conductive structure, and electrically energizing the structure for electrocautery.

\* \* \* \* \*